US008609372B2

(12) United States Patent
Meador, III

(10) Patent No.: US 8,609,372 B2
(45) Date of Patent: Dec. 17, 2013

(54) GLYCOSYL TRANSFERASE FROM CHINESE HAMSTER AND RELATED METHODS

(75) Inventor: James W. Meador, III, Framingham, MA (US)

(73) Assignee: Momenta Pharmaceuticals, Inc., Cambridge, MA (US)

(*) Notice: Subject to any disclaimer, the term of this patent is extended or adjusted under 35 U.S.C. 154(b) by 199 days.

(21) Appl. No.: 12/943,719

(22) Filed: Nov. 10, 2010

(65) Prior Publication Data

US 2011/0275526 A1 Nov. 10, 2011

Related U.S. Application Data

(60) Provisional application No. 61/260,232, filed on Nov. 11, 2009.

(51) Int. Cl.
| | | |
|---|---|---|
| C12P 21/02 | (2006.01) | |
| C07H 21/04 | (2006.01) | |
| C12N 5/10 | (2006.01) | |
| C12N 15/00 | (2006.01) | |

(52) U.S. Cl.
USPC ..... 435/69.1; 435/6.11; 435/70.3; 435/320.1; 435/358; 536/23.2; 536/23.4; 536/23.5

(58) Field of Classification Search
None
See application file for complete search history.

(56) References Cited

U.S. PATENT DOCUMENTS

| | | | |
|---|---|---|---|
| 5,143,854 A | 9/1992 | Pirrung et al. | |
| 5,288,514 A | 2/1994 | Ellman | |
| 5,324,663 A * | 6/1994 | Lowe | 435/320.1 |
| 5,384,261 A | 1/1995 | Winkler et al. | |
| 5,510,270 A | 4/1996 | Fodor et al. | |
| 5,527,681 A | 6/1996 | Holmes | |
| 5,695,937 A | 12/1997 | Kinzler et al. | |
| 5,849,991 A | 12/1998 | d'Apice et al. | |
| 5,955,347 A | 9/1999 | Lowe | |
| 5,985,551 A * | 11/1999 | Brennan | 435/6.11 |
| 6,713,055 B2 | 3/2004 | Schiff | |
| 2005/0214823 A1 * | 9/2005 | Blume et al. | 435/6 |

FOREIGN PATENT DOCUMENTS

| | | |
|---|---|---|
| KR | 1020040017947 * | 2/2004 |
| WO | WO 93/22684 | 11/1993 |
| WO | WO-9524924 A1 | 9/1995 |
| WO | WO 0130992 A2 * | 5/2001 |
| WO | WO 2008/130926 | 10/2008 |
| WO | WO 2010/085251 | 7/2010 |

OTHER PUBLICATIONS

GenBank Accession No. DI048260.1. GI: 168293398, publicly available Feb. 2008.*
Cabrita et al. A family of E. coli expression vectors for laboratory scale and high throughput soluble protein production. BMC Biotechnology, vol. 6, p. 12, 2006, printed as pp. 1/8 to 8/8.*
GenBank AF520589.1, GI: 21686557, Jul. 2002, printed as pp. 1/2-2/2.*
Anumula, Kalyan R., "Advances in fluorescence derivatizatio methods for high-performance liquid chromotographic analysis of glycoprotein carbohydrates," Anal. Biochem. 350(1), pp. 1-23, 2006.
Ashford , et al., "Site-specific Glycosylation of Recombinant Rat and Human Soluble CD4 Variants Expressed in Chinese Hamster Ovary Cells," The Journal of Biological Chemistry, vol. 268(5), pp. 3260-3267, 1993.
Baker, K.N., et al., "Metabolic control of recombinant protein N-glycan processing in NS0 and CHO cells," Biotechnol Bioeng 73, pp. 188-202, 2001.
Beck, A., et al., "Trends in glycosylation, glycoanalysis and glycoengineering of therapeutic antibodies and Fc-fusion proteins," Curr Pharm Biotechnol 9, pp. 482-501, 2008.
Bhindi et al., "Brothers in arms: DNA enzymes, short interfering RNA, and the emerging wave of small-molecule nucleic acid-based gene-silencing strategies," Am J Pathol. 171(4), pp. 1079-1088, 2007.
Bosques, et al., "Chinese hamster ovary cells can produce galactose-α-1, 3-galactose antigens on proteins," Nature Biotechnology, vol. 28(11), pp. 1153-1156, 2010.
Carr, S.A., et al., "Protein and carbohydrate structural analysis of a recombinant soluble CD4 receptor by mass spectrometry," J Biol Chem 264, pp. 21286-21295, 1989.
Urlaub et al., "Isolation of Chinese hamster cell mutants deficient in dihydrofolate reductase activity," Proc. Natl. Acad. Sci. USA 77(7), pp. 4216-4220, 1980.
Chung, C.H., et al., "Cetuximab-induced anaphylaxis and IgE specific for galactose-alpha-1,3-galactose," N Engl J Med 358,pp. 119-1117, 2008.
Davidson, D.J. & Castellino, F.J., "Oligosaccharide structures present on asparagine-289 of recombinant human plasminogen expressed in a Chinese hamster ovary cell line," Biochemistry 30, pp. 625-633, 1991.
Deglon Nicole et al., "Presence of Gal-alpha 1, 3Gal epitope on xenogeneic lines: implications for cellular gene therapy based on the encapsulation technology", Xenotransplantation, vol. 10, No. 3, pp. 204-213, May 2003.
Hara et al., "Determination of Mono-O-acetylated N-Acetylneuraminic Acids in Human and Rat Ssera by Fluorometric High-Performance Liquid Chromotography," Anal. Biochem., 179, pp. 162-166, 1989.
Hong, J.K., Cho, S.M. & Yoon, S.K., "Substitution of glutamine by glutamate enhances production and galactosylation of recombinant IgG in Chinese hamster ovary cells," Appl Microbiol Biotechnol 88, pp. 869-876, 2010.
Jefferis, R., "Glycosylation as a strategy to improve antibody-based therapeutics," Nat Rev Drug Discov 8, pp. 226-234, 2009.
Jenkins, N., Parekh, R.B. & James, D.C., "Getting the glycosylation right: implications for the biotechnology industry," Nat Biotechnol 14, pp. 975-981, 1996.
Kagawa, Y., et al., "Comparative study of the asparagine-linked sugar chains of natural human interferon-beta 1 and recombinant human interferon-beta 1 produced by three different mammalian cells," J Biol Chem 263, pp. 17508-17515, 1988.

(Continued)

Primary Examiner — Jennifer Dunston
(74) Attorney, Agent, or Firm — Choate, Hall & Stewart LLP; Brenda H. Jarrell; Rolando Medina

(57) ABSTRACT

A glycosyl transferase from Chinese hamster and related methods are described.

27 Claims, 19 Drawing Sheets

(56) References Cited

OTHER PUBLICATIONS

Kumpel, B.M., Rademacher, T.W., Rook, G.A., Williams, P.J. & Wilson, I.B., "Galactosylation of human IgG monoclonal anti-D produced by EBV-transformed B-lymphoblastoid cell lines is dependent on culture method and affects Fc receptor-mediated functional activity," *Hum Antibodies Hybridomas* 5, pp. 143-151, 1994.

Macher, B.A. & Galili, U., "The Galalphal,3Galbeta1,4G1cNAc-R (alpha-Gal) epitope: a carbohydrate of unique evolution and clinical relevance," *Biochim Biophys Acta* 1780, pp. 75-88, 2008.

Pan and Clawson, "Antisense applications for biological control," *J. Cell Biochem.* 98(1), pp. 14-35, 2006.

Parekh, R.B., et al., "N-glycosylation and in vitro enzymatic activity of human recombinant tissue plasminogen activator expressed in Chinese hamster ovary cells and a murine cell line," *Biochemistry* 28, pp. 7670-7679, 1989.

Potvin, et al., "Transfection of a Human α-(1,3) Fucosyltransferase Gene into Chinese Hamster Ovary Cells. Complications arise from activation of endogenoius alpha-(1,3) fucosyltransferases," *The Journal of Biological Chemistry*, vol. 265(3), pp. 1615-1622, 1990.

Sasaki, H., Bothner, B., Dell, A. & Fukuda, M., "Carbohydrate structure of erythropoietin expressed in Chinese hamster ovary cells by a human erythropoietin cDNA," *J Biol Chem* 262, pp. 12059-12076, 1987.

Shah, et al., "Active site studies of bovine α1 → 3-galactosyltransferase and its secondary structure prediction," *Biochim Biophys Acta*, 1480(1-2): pp. 222-234, 2000.

Sheeley, D.M., Merrill, B.M. & Taylor, L.C., "Characterization of monoclonal antibody glycosylation: comparison of expression systems and identification of terminal alpha-linked galactose," *Anal Biochem* 247, pp. 102-110, 1997.

Sioud and Iversen, "Ribozymes, DNAzymes and small interfering RNAs as therapeutics," *Curr Drug Targets* 6(6), pp. 647-653, 2005.

Smith, D.F., Larsen, R.D., Mattox, S., Lowe, J.B. & Cummings, R.D., "Transfer and expression of a murine UDP-Gal:beta-D-Gal-alpha 1,3-galactosyltransferase gene in transfected Chinese hamster ovary cells. Competition reactions between the alpha 1,3-galactosyltransferase and the endogenous alpha 2,3-sialyltransferase," *J Biol Chem* 265, pp. 6225-6234, 1990.

Spellman, M.W., et al., "Carbohydrate structures of human tissue plasminogen activator expressed in Chinese hamster ovary cells," *J Biol Chem* 264, pp. 14100-14111, 1989.

Spellman, M.W., Leonard, C.K., Basa, L.J., Gelineo, I. & van Halbeek, H., "Carbohydrate structures of recombinant soluble human CD4 expressed in Chinese hamster ovary cells," *Biochemistry* 30, pp. 2395-2406, 1991.

Srinivas et al., "Pharmacokinetics and Pharmacodynamics of CTLA4Ig (BMS-188667), a Novel Immunosuppressive Agent, in Monkeys following Multiple Doses," *J. Pharm. Sci.* 85(1), pp. 1-4, 1996.

Srinivas et al., "Assessment of Dose Proportionality, Absolute Bioavailability, and Immunogenicity Response of CTLA4Ig (BMS-188667), a Novel Immunosuppressive Agent, Following Subcutaneous and Intravenous Administration to Rats," *Pharm. Res.* 14(7), pp. 911-916, 1997.

Stadlmann et al., "Analysis of immunoglobulin glycosylation by LC-ESI-MS of glycopeptides and oligosaccharides," *Proteomics*, 8(14), pp. 2858-2971, 2008.

Takeuchi, M., et al., "Comparative study of the asparagine-linked sugar chains of human erythropoietins purified from urine and the culture medium of recombinant Chinese hamster ovary cells," *J Biol Chem* 263, pp. 3657-3663, 1988.

Takeuchi, et al., "Relationship between sugar chain structure and biological activity of recombinant human erythropoietin produced in Chinese hamster ovary cells," *Proc Natl Acad Sci USA* 86, pp. 7819-7822, 1989.

Taylor, et al., "Characterization of the rat α(1,3)galactosyltransferase: evidence fro two independent genes encoding glycosylatransferases that syntheseize Galα(1,3)Gal by two separate glycosylation pathways," *Glycobiology*, 13, pp. 327-337, 2003.

Townsend, R.R., "Analysis of Glycoconjugates Using High-pH Anion-Exchange Chromatography," *Dep. of Pharm. Chem*, 5, pp. 181-209, 1995.

Weiner et al., "A sensitive enzyme immunoassay for the quantitation of human CTLA4Ig fusion protein in mouse serum: pharmacokinetic application to optimizing cell line selection," *J Pharm Biomed Anal.* 15(5), pp. 571-579, 1997.

Wurm, "Production of recombinant protein therapeutics in cultivated mammalian cells," *Nature Biotech.* 22, pp. 1393-1398, 2004.

Yamane-Ohnuki et al., Establishment of FUT8 Knockout Chinese Hamster Ovary Cells: An Ideal Host Cell Line for Producing Completely Defucosylated Antibodies With Enhanced Antibody-Dependent Cellular Cytotoxicity, *Biotechnol. Bioeng* 87, pp. 614-622, 2004.

Yuen, C.T., Carr, S.A. & Feizi, T., "The spectrum of N-linked oligosaccharide structures detected by enzymic microsequencing on a recombinant soluble CD4 glycoprotein from Chinese hamster ovary cells," *Eur J Biochem* 192, pp. 523-528, 1990.

GenBank Accession No. AAO49077: alpha-1,3-galactosyltransferase [Rattus norvegicus] (Apr. 23, 2003).

International Search Report for PCT/US2010/056230 dated Sep. 26, 2011.

Written Opinion for PCT/US2010/056230 dated Sep. 26, 2011.

Koike, et al., Functionally Important Glycosyltransferase Gain and Loss During Cararrhine Primate Emergence, PNAS, 104(2):559-564 (2007).

Larsen, et al., Isolation of a cDNA Encoding a Murine UDPgalactose: β-D-galactosyl-1,4-N-acetyl-D-glucosaminide α-1,3-galactosyltransferase: Expression Cloning by Gene Transfer, PNAS, 86:8227-8231 (1989).

\* cited by examiner

*Ggta1-a*

```
SEQ ID NO:1: ATG AAT GTC AAG GGA AAA GTG GTC CTG TCG ATG CTG GTT GTC TCA ACT GTG CTT GTC GTG  60
SEQ ID NO:2:  M   N   V   K   G   K   V   V   L   S   M   L   V   V   S   T   V   L   V   V   20

61 TTT TGG GAA TAT GTC AAC AGC CCA GAA GGT TCC TTC TTG TGG ATA TAT CAC ATG AAA ATT 120
         21  F   W   E   Y   V   N   S   P   E   G   S   F   L   W   I   Y   H   M   K   I   40

121 CCA GAG ATT GGT GAC AGC AGC AGG CAG AGC TGG TGG TTC CCG AGC TGG TTT AGC AAT GGG 180
         41  P   E   I   G   D   S   S   R   Q   S   W   W   F   P   S   W   F   S   N   G   60

181 ACC CAC AGT TAT CAA GAA GAG GAC gTA GAA AGA GGG AGA GAA AAG CAG CGA AAT GCA GTC 240
         61  T   H   S   Y   Q   E   E   D   V   E   R   G   R   E   K   Q   R   N   A   V   80

241 AGA ATT GAA GAG CCT CAC TTG TGG GAC TGG TTT AAT CCA AAG AAC CGC CCA GAA GTT TTG 300
         81  R   I   E   E   P   H   L   W   D   W   F   N   P   K   N   R   P   E   V   L  100

301 ACA GTG ACC CCA TGG AAG GCA CCA ATT GTG TGG GAA GGC ACT TAT GAC AGA GCT ATG CTG 360
        101  T   V   T   P   W   K   A   P   I   V   W   E   G   T   Y   D   R   A   M   L  120

361 GAA AAG TAT TAc GCC AGA CAG AAA ATC ACC GTG GGA CTG ACA GTT TTT GCT GTG GGA AAG 420
        121  E   K   Y   Y   A   R   Q   K   I   T   V   G   L   T   V   F   A   V   G   K  140
```

FIGURE 3-2

```
421 TAC Att GAG CAT TAT TTG GAA GAT TTC CTg GAG TCT GCT AGC AGG TAC TTC ATG GTT GGC 480
141  Y   I   E   H   Y   L   E   D   F   L   E   S   A   S   R   Y   F   M   V   G  160

481 CAC AGG GTC ATA TTT TAT GTC ATG ATG GAC GAT GCC TCC AGA ATG CCT TTT ATA CAC CTG 540
161  H   R   V   I   F   Y   V   M   M   D   D   A   S   R   M   P   F   I   H   L  180

541 AGT CCT CTG CAT TCC TTA CAA GTG TTT GAG ATC AAG TCT GAG ACC AGG TGG CAA GAC ATT 600
181  S   P   L   H   S   L   Q   V   F   E   I   K   S   E   T   R   W   Q   D   I  200

601 AGC ATG ATG CGC ATG AAG ACA ATC GAG GAG CAC ATC CTG ACC CAC ATA CAG CAT GAG GTC 660
201  S   M   M   R   M   K   T   I   E   E   H   I   L   T   H   I   Q   H   E   V  220

661 GAC TTC CTC TTC TGT ATG GAC GTG GAT CAG GTC TTT CAA GAC AAT TTT GGA GTG GAG ACT 720
221  D   F   L   F   C   M   D   V   D   Q   V   F   Q   D   N   F   G   V   E   T  240

721 CTG GGC CAG TTG GTA GCT CAG CTC CAG GCC TGG TGG TAC AAA GCT GAC Cat GAC AAG TTT 780
241  L   G   Q   L   V   A   Q   L   Q   A   W   W   Y   K   A   D   H   D   K   F  260
```

FIGURE 3-3

```
781  ACC TAT GAG AGG CGG GAA CTG TCG GCG GCA TAC ATC CCA TTT GGA CAG GGG GAT TTT TAT  840
261   T   Y   E   R   R   E   L   S   A   A   Y   I   P   F   G   Q   G   D   F   Y   280

841  TAC Cac GCA GCC ATT TTC GGA GGG ACA CCC ATT CAT ATT CTC AAC CTC ACC CGG GAG TGC  900
281   Y   H   A   A   I   F   G   G   T   P   I   H   I   L   N   L   T   R   E   C   300

901  TTT GAG GGG ATC CTC CAG GAC AAG AAC AAC AAC ATA GAA GCA AAG TGG CAT GAC GAA AGT  960
301   F   E   G   I   L   Q   D   K   N   N   N   I   E   A   K   W   H   D   E   S   320

961  CAC CTA AAC AAA TAT TTC CTT TTC AAC AAG CCC ACT AAA ATT TTA TCT CCA GAG TAC TGT  1020
321   H   L   N   K   Y   F   L   F   N   K   P   T   K   I   L   S   P   E   Y   C   340

1021 TGG GAC TAT CAG ATA GGC TTG CCT TCA GAA ATT AAA AAT GTA AAG ATA GCT TGG CAG ACA  1080
341   W   D   Y   Q   I   G   L   P   S   E   I   K   N   V   K   I   A   W   Q   T   360

1081 AAA GAG TAT AAT TTG GTT AGG AGT AAT GTC  1110
361   K   E   Y   N   L   V   R   S   N   V   370
```

FIGURE 4-1

*Ggta1-b*

```
SEQ ID NO:3:   ATG AAT GTC AAG GGA AAA GTG GTC CTG TCG ATG CTG GTT GTC TCA ACT GTG CTT GTC GTG  60
SEQ ID NO:4:    M   N   V   K   G   K   V   V   L   S   M   L   V   V   S   T   V   L   V   V   20

61  TTT TGG GAA TAT GTC AAC AGC CCA GAA GGT TCC TTC TTG TGG ATA TAT CAC ATG AAA ATT 120
           21   F   W   E   Y   V   N   S   P   E   G   S   F   L   W   I   Y   H   M   K   I   40

121  CCA GAG ATT GGT GAC AGC AGC AGG CAG AGC TGG TGG TTC CCG AGC TGG TTT AGC AAT GGG 180
           41   P   E   I   G   D   S   S   R   Q   S   W   W   F   P   S   W   F   S   N   G   60

181  ACC CAC AGT TAT CAA GAA GAG GAC ATA GAA AGA GGG AGA GAA AAG CAG CGA AAT GCA GTC 240
           61   T   H   S   Y   Q   E   E   D   I   E   R   G   R   E   K   Q   R   N   A   V   80

241  AGA ATT GAA GAG CCT CAC TTG TGG GAC TGG TTT AAT CCA AAG AAC CGC CCA GAA GTT TTG 300
           81   R   I   E   E   P   H   L   W   D   W   F   N   P   K   N   R   P   E   V   L  100

301  ACA GTG ACC CCA TGG AAG GCA CCA ATT GTG TGG GAA GGC ACT TAT GAC AGA GCT ATG CTG 360
          101   T   V   T   P   W   K   A   P   I   V   W   E   G   T   Y   D   R   A   M   L  120

361  GAA AAG TAT TAT GCC AGA CAG AAA ATC ACC GTG GGA CTG ACA GTT TTT GCT GTG GGA AAG 420
          121   E   K   Y   Y   A   R   Q   K   I   T   V   G   L   T   V   F   A   V   G   K  140
```

FIGURE 4-2

```
421 TAC ATC GAG CAT TAT TTG GAA GAT TTC CTA GAG TCT GCT AGC AGG TAC TTC ATG GTT GGC  480
141  Y   I   E   H   Y   L   E   D   F   L   E   S   A   S   R   Y   F   M   V   G   160

481 CAC AGG GTC ATA TTT TAT GTC ATG ATG GAC GAT GCC TCC AGA ATG CCT TTT ATA CAC CTG  540
161  H   R   V   I   F   Y   V   M   M   D   D   A   S   R   M   P   F   I   H   L   180

541 AGT CCT CTG CAT TCC TTA CAA GTG TTT GAG ATC AAG TCT GAG ACC AGG TGG CAA GAC ATT  600
181  S   P   L   H   S   L   Q   V   F   E   I   K   S   E   T   R   W   Q   D   I   200

601 AGC ATG ATG CGC ATG AAG ACA ATC GAG GAG CAC ATC CTG ACC CAC ATA CAG CAT GAG GTC  660
201  S   M   M   R   M   K   T   I   E   E   H   I   L   T   H   I   Q   H   E   V   220

661 GAC TTC CTC TTC TGT ATG GAC GTG GAT CAG GTC TTT CAA GAC AAT TTT GGA GTG GAG ACT  720
221  D   F   L   F   C   M   D   V   D   Q   V   F   Q   D   N   F   G   V   E   T   240
```

FIGURE 4-3

```
721  CTG GGC CAG TTG GTA GCT CAG CTC CAG GCC TGG TGG TAC AAA GCT GAC CAC GAC AAG TTT  780
241   L   G   Q   L   V   A   Q   L   Q   A   W   W   Y   K   A   D   H   D   K   F   260

781  ACC TAT GAG AGG CGG GAA CTG TCG GCG GCA TAC ATC CCA TTT GGA CAG GGG GAT TTT TAT  840
261   T   Y   E   R   R   E   L   S   A   A   Y   I   P   F   G   Q   G   D   F   Y   280

841  TAC CAT GCA GCC ATT TTC GGA GGG ACA CCC ATT CAT ATT CTC AAC CTC ACC CGG GAG TGC  900
281   Y   H   A   A   I   F   G   G   T   P   I   H   I   L   N   L   T   R   E   C   300

901  TTT GAG GGG ATC CTC CAG GAC AAG AAC AAC AAC ATA GAA GCA AAG TGG CAT GAC GAA AGT  960
301   F   E   G   I   L   Q   D   K   N   N   N   I   E   A   K   W   H   D   E   S   320

961  CAC CTA AAC AAA TAT TTC CTT TTC AAC AAG CCC ACT AAA ATT TTA TCT CCA GAG TAC TGT  1020
321   H   L   N   K   Y   F   L   F   N   K   P   T   K   I   L   S   P   E   Y   C   340

1021 TGG GAC TAT CAG ATA GGC TTG CCT TCA GAA ATT AAA AAT GTA AAG ATA GCT TGG CAG ACA  1080
341   W   D   Y   Q   I   G   L   P   S   E   I   K   N   V   K   I   A   W   Q   T   360

1081 AAA GAG TAT AAT TTG GTT AGG AGT AAT GTC  1110
361   K   E   Y   N   L   V   R   S   N   V   370
```

FIGURE 5-1

*partial Ggta1 genomic sequence from CHO cell line (SEQ ID NO:5)*

GAACCGCCCAGAAGTTTTGACAGTGACCCCATGGAAGGCGCCAATTGTGTGGGAAGGCACTTATGACAGAGCTCTGCTGGAAAAGTATTATGCCAGACAGAAAATCAC

CGTGGGGCTGACGGTTTTTGCTGTGGGAAAGTaagcaaaaatgacaaacttgcccttgatttttttttcttgttttaccatcaaagtcattgtgagggacccgtagc cctacagaagcctcccttacttgagttactaggaaggagacttccatttcctttctgatgacagctgaggagcaaaatcaatagtaggtaagtccacccatcccac cacagaacggagagaactgtcttcagtgccaccggaacccagagctaagagcatgcctgccgctccctcctccctgaccTctagggctttcctagggaggcccaaat gccagctgttaatgcccaggaccaaggacggggttagaagttgtggagtgtgctctgtgctccatggtttccaggctgacatgtggctgctgctctctcatgggccc tctggtcctgtctactggaccttcccggaggatttgaccctggtgttggatgatcagaacctgctgagcctggacaggtcctggctgcagcagcttccacttcctnat ttagagctggatgcagaaacattgtactcattcttgaagctatgccattggttttagtctaacccatcttgtttcttagtgcattaaccatttttccctaaactaaa acattaggtttatattttcaatctttttccctttcttctttctttctttctttctttctntcnttcttttctgaggcagagttgcatttttaaggatgtcttaag aaaggaaaagtcaggattatgagagagccaccaacaaagtaagacatattggagagtgtgtgagtgtaggcttctctgagagaatcaccctctgcttaaaaaaaaaa aaaaaagttttgtatctagtgtgtgtgtgtaggtcagaggatgactttcaggagttggctctctctctactatgtggttctggggatccaacttaagtcttcagg cttggcagcaagtgcccttacatactgagaatcctgctgttatgtttcttttctgccctctgagcctcTgtgttggaaccttatgaaaagtgacaaaatcaac aggatgttgactcccctgccatgttcaaaaggagtagaaggggcagtttggcctgaccttgatctttgacaagaacctaaaagacagcaccgtgatgatgccacaggg cccccacagcgcccagtgctgtctttgggaaatttagcattgctcagtgtgctgagtccctggggtccaatggcatcccaatgggaaacagtggctgtggagttcgg acatttcactagaagaatttgtattttttaggggtgggattcaaggctcaacttagcaaacacttctggcacagaagggaaagacagctatattacacattgatttgat ccccaaagaacaaaatgaacccactgtctcacaatGgctatcaaccatccaattacaacttcgcaggaaaatagaaaacaaaacaataaaaaaaagtcctacgactgc ctcccacttcctggtgaaagccgtgctcccagctaggccagtctgcagtggtgaatcccagaggaaatgcaccggaccccgggaggtgtgacttttgctttgcttt ttatctcagtgcctggagtcaactgtgataccttaaccccttaaacatcctcagatgtcacagtgacactgccctacactcccctaagcat

FIGURE 5-2 tgtttccccgaacttcaggcacactagttttttcttgaagttcagagtacagaagtctgtcttgacctccagccatggagtcatgtcagagctctcttttaccactggg atatatttgccccacccaaagaatcagtactagaaaccttgagctttgcaatgccaacagtaaaagtgaaatttatttccatggcaaacaacaacccaagcatcaaga aaaacaaaacagagattggagagatggctcagtggttgatagtattggctgccttctagtggacccagggttcaattcccagcactcacatggtgtcaggaaaaagg gcagccaaagaaacacacttggtccctgcaatcagacccagagaaagaaatacatcctggccctaaaattagagccaaaagactaaaaaggaccagtcaaacaaacat actttgccctgaaaccagagccaaatctgaccctaatcctgtgcagaaaaccaaccaatccctgaGcaggagatttagccattcagacctcagggattgaaatctgg ccaatcccaccctggaaatctccctggaaaaactcccctaagattcccatataaacccgtatc tgttcagcttctggctgcctggattcttccctcccaataaatctcttcaatgatgtttgaggtgagaccttctttcaccagagagcagatcggagtacggctgtaaca ctttgctgctctccttgcccaactgtaacaactttaccagggaagccctctcctgcaggagcagagctgatacactgggaagccgt tccctgaagcagggctgtaagctgctatccttactgtgacctgtggtattccttggctccgatgccagaatacctttccatctgagctgtaacactcagtattctt cggctttcaagtgccgtaatccatcccatccgatctgtcaaaatgcttacacatggcagctacaactgtctgtaactccagttccagcggatctggcaactccacac aggcatacacactagcaaaacacaaatgcacataaaaataaattattggaaaaaaaagagaaaatgcaagtattt

FIGURE 5-3 tttaaaaaagaaaaaaacactagtcattctgcttggctagttgtgtgctcagtaaactgtcgtccgtagtctctgtgtctaagtttgaggtttggaaagggaccatct gacttcccctcatctctgcagtctccttggcatgaattaggaaaatagtctgtagcttgagcttgtataaggcatcactataatgtcactcaaatgataaatagaca aattgacaaatctcatctgttagaatggcaaaaaaaaaaaaaaaaactgccaataccaaatgttgaaaaggtctgaactaatcagaatccttgttactgctagtgg gaatataatatggtacagccatcttgggagaaatttbggcagttgcttgcaaaattgagcatgctctbatcaatctaatcatcaaattccttggtattaacccaag tgagttcaaaaagtcttacacaaaaacctgcatatagatattcttaaaagctttattcataattgctaaaacttgggaccagacaagttttccttbgacaggcaaatg taaaaaatgaattgtggtccattcagataacagaatattattcattctgctaaaaagtgacctatgaagccatagaaaccaaggagaaatttttgtcactaagtgaag aacctaatctgggaaggttcctatgctgtcagtattatatcaccttgtcacagctggaggcaccagagaggagcagcctcagatcaggctgcagggcattttctaatg actaattgatggaggagagcccagcccattgtggtggagctatccctggcctggtggtcctgtattctataacaaagcagactaagacatcagggacaagccataag cagcacacctccatggcttctgcatcagcttctgcctccaggttcctaccctgtttgagttcctgtcatgtcacttcactgggttactatgtgaatgtgtgagccaaa taattttccttctgaacttgcttttggtgttggtgttccaccaagggcaacagtaaccttatgacaggtccatactgcctgctttggattctgattctggaagaggc aaaactatagtgttaggaacaagattattgactcaagagctgggggagagaggaggagaaaagaagagcctagaagattcttagggtagtgaagctattctgaatgat accacagcggtggatatgcctggcattgtgcttttgcacatttcccaaagtgaaccttagtagaaactatgttctcagtggaagtgacaactattacaaacctgctgt ctggagcatggtggtcctactaggaaggttgttcattctgtctaggcaggacgcatttgggtactcccaaactttcagctcagttttgctcacaattcaaaatacagaa gtattaaaatatagccagactgtagctagatcgttgactaagctttgcagtggagctctaggtttgatcccacgtaccacaaaaactgcacgtgttgtggcatgttt gtaatcctagcaggagtatcagaagttgaaggtcatcttggctgcatagtgagttgagcctagcctgacatacatgataacctgtctcaaaaaaaaaagttaaatt aagagaatcagagactgttccagtattggatcgatttgtaacatcattatttgtctggatgatacactggtgtttgacgtaaccagtaggaggtttgtagaatggcc aggcaatgtgggatttccatcttccaccattccctgcatcacagaggatcatgggacggtgccggtgggagtcgatctccatcctacacaccattcctcgtatcaca aaggagcgtgggacagtgctatgcttagacttaacaaaacacagagaagataaggttgttatgaatgcccgctcgacatgggcagcatac

FIGURE 5-4 ttgctttgcatttggcctggcagtagcgacactggcctcagcgtattccacggctacacctcctttgatggcaggcttccaaatttgagaacagacccttaccgtgac
gcttactgcaaagcgggtagttgaaaacacatacctctcagcctcgcctgcttccaagagcaggaggacagggctatgcatgcccagttgttcttacagagttgccac
tggcagaagttattccactttccctgaggactcggaaacgaccacctcgtcgacagcagccagggtgctgaactagcatgtgtccccgtaagggtactagtcatcgtt
aaacatgtccccctctgtttcaggtACATAGAGCATTATTTGGAAGATTCTCGGAGTCTGCTAACAGGTACTTCATGGTTGGCCACAGGGTCATATTTTATGTCATG
GTGGACGATGCCTCCAGAATGCCTTCTATACACCTGAGTCCTCTGCATTCCTTACAAGTGTTTGAGATCAAGTCCGAGAAGCGATGGCAGGACATCAGCATGATGCGG
ATGAAGACCATCGGGGAGCACATCCTGTCCCACATACAGCACGAGGTCGACTTCCTCTTCTGCATGGACGTGGATCAGGTCTTTCAAGACAATTTCGGTGTGGAGACT
CTGGGCCAGTTGGTAGCTCAGCTCCAGGCCTGGTGGTACAAGGCCGATCGTGACAAGTTTACCTATGAGACGCGGAAACTGTCGGCGGCGTACATCCCGTTTGGGCAG
GGGGATTTTTATTACCACGCAGCCATTTTTGGAGGAACACCCATTCACATTCTCAACCTCACCCGAGAGTGCTTTGAGGGAATCCTCCAGGACAAGAGCAATGACATC
GAAGCAGAGTGGCACGATGAGAGCCACCTCAACAAATACTTCCTTTTCAACAAACCCACTAAAATCTTATCTCCAGAATACTGTTGGGACTATCAGATAGGCTTGCCT
TCAGAAATTAAAAATGTAAAGGTAGCCTGGCAGACAAAAGAGTATAATTTGGTTAGGAGTAATGTCTGA

FIGURE 6-1

*Ggta1 exon 8 and 9*

```
SEQ ID NO:6: AAC CGC CCA GAA GTT TTG ACA GTG ACC CCA ATT GTG TGG GAA GGC ACT    60
SEQ ID NO:7:  N   R   P   E   V   L   T   V   T   P   I   V   W   E   G   T    20

61 TAT GAC AGA GCT CTG CTG GAA AAG TAT TAT GCC AGA CAG AAA GCG CCA ATC ACC GTG GGG CTG ACG  120
 21  Y   D   R   A   L   L   E   K   Y   Y   A   R   Q   K   A   P   I   T   V   G   L   T   40

121 GTT TTT GCT GTG GGA AAG TAC ATA GAG CAT TAT TTG GAA GAT TTT CTG GAG TCT GCT AAC  180
 41  V   F   A   V   G   K   Y   I   E   H   Y   L   E   D   F   L   E   S   A   N   60

181 AGG TAC TTC ATG GTT GGC CAC AGG GTC ATA TTT TAT GTC ATG ATG GAT GAT GCC TCC AGA  240
 61  R   Y   F   M   V   G   H   R   V   I   F   Y   V   M   M   D   D   A   S   R   80

241 ATG CCT TCT ATA CAC CTG AGT CCT CAT CTG TCC TTA CAA GTG TTT GAG ATC AAG TCC GAG  300
 81  M   P   S   I   H   L   S   P   H   L   S   L   Q   V   F   E   I   K   S   E  100

301 AAG CGA TGG CAG GAC ATC AGC ATG ATG CGG ATG AAG ACC ATC GGG GAG CAC ATC CTG TCC  360
101  K   R   W   Q   D   I   S   M   M   R   M   K   T   I   G   E   H   I   L   S  120

361 CAC ATA CAG CAC GAG GTC GAC TTC CTC TGC TTC ATG GAC GTG GAT CAG GTC TTT CAA GAC  420
121  H   I   Q   H   E   V   D   F   L   C   F   M   D   V   D   Q   V   F   Q   D  140
```

FIGURE 6-2

```
421 AAT TTC GGT GTG GAG ACT CTG GGC CAG TTG GTA GCT CAG CTC CAG GCC TGG TAC AAG 480
141  N   F   G   V   E   T   L   G   Q   L   V   A   Q   L   Q   A   W   Y   K  160

481 GCC GAT CGT GAC AAG TTT ACC TAT GAG AGG CGG AAA CTG TCG GCG GCG TAC ATC CCG TTT 540
161  A   D   R   D   K   F   T   Y   E   R   R   K   L   S   A   A   Y   I   P   F  180

541 GGG CAG GGG GAT TTT TAT TAC CAC GCA GCC ATT TTT GGA ACA CCC ATT CAC ATT CTC 600
181  G   Q   G   D   F   Y   Y   H   A   A   I   F   G   T   P   I   H   I   L  200

601 AAC CTC ACC CGA GAG TGC TTT GAG GGA ATC CTC CAG AAG AGC AAT GAC ATC GAA GCA 660
201  N   L   T   R   E   C   F   E   G   I   L   Q   K   S   N   D   I   E   A  220

661 GAG TGG CAC GAT GAG CAC AGC CTC CAG TTC CTT TTC AAC AAA CCC ACT AAA ATC 720
221  E   W   H   D   E   H   S   L   Q   F   L   F   N   K   P   T   K   I  240

721 TTA TCT CCA GAA TAC TGT TGG GAC TAT CAG ATA GGC TTG CCT TCA GAA ATT AAA AAT GTA 780
241  L   S   P   E   Y   C   W   D   Y   Q   I   G   L   P   S   E   I   K   N   V  260

781 AAG GTA GCC TGG CAG ACA AAA GAG TAT AAT TTG GTT AGG AGT AAT GTC 828
261  K   V   A   W   Q   T   K   E   Y   N   L   V   R   S   N   V  276
```

Lanes
1 = E-Gel Low Range DNA ladder
2 = Ggta1 (154-4) top standard (A1)*
3 = CL 33 (A3)
4 = CL 33 (A4)
5 = CL 34 (A5)
6 = CL 34 (A6)
7 = CL 1 (A7)
8 = CL 1 (A8)
9 = CL 33 No RT control (E3)
10 = CL 34 No RT control (E5)
11 = CL1 No RT control (E7)
12 = E-Gel Low Range DNA ladder

*refers to sample position on the 96-well plate.

SEQUENCE LISTING

```
<160> NUMBER OF SEQ ID NOS: 59

<210> SEQ ID NO 1
<211> LENGTH: 1110
<212> TYPE: DNA
<213> ORGANISM: Cricetulus griseus

<400> SEQUENCE: 1
atgaatgtca agggaaaagt ggtcctgtcg atgctggttg tctcaactgt gcttgtcgtg      60
ttttgggaat atgtcaacag cccagaaggt tccttcttgt ggatatatca catgaaaatt     120
ccagagattg gtgacagcag caggcagagc tggtggttcc cgagctggtt tagcaatggg     180
acccacagtt atcaagaaga ggacgtagaa agagggagag aaaagcagcg aaatgcagtc     240
agaattgaag agcctcactt gtgggactgg tttaatccaa agaaccgccc agaagttttg     300
acagtgaccc catggaaggc accaattgtg tgggaaggca cttatgacag agctatgctg     360
gaaaagtatt acgccagaca gaaaatcacc gtgggactga cagtttttgc tgtgggaaag     420
tacattgagc attatttgga agatttcctg gagtctgcta gcaggtactt catggttggc     480
cacagggtca tattttatgt catgatggac gatgcctcca gaatgccttt tatacacctg     540
agtcctctgc attccttaca agtgtttgag atcaagtctg agaccaggtg gcaagacatt     600
agcatgatgc gcatgaagac aatcgaggag cacatcctga cccacataca gcatgaggtc     660
gacttcctct tctgtatgga cgtggatcag gtctttcaag acaatttggg agtggagact     720
ctgggccagt tggtagctca gctccaggcc tggtggtaca aagctgacca tgacaagttt     780
acctatgaga ggcgggaact gtcggcggca tacatcccat ttggacaggg ggattttttat     840 taccacgcag ccatttttcgg agggacaccc attcatattc tcaacctcac ccgggagtgc     900
tttgagggga tcctccagga caagaacaac aacatagaag caaagtggca tgacgaaagt     960
cacctaaaca aatatttcct tttcaacaag cccactaaaa ttttatctcc agagtactgt    1020
tgggactatc agataggctt gccttcagaa attaaaaatg taaagatagc ttggcagaca    1080
aaagagtata atttggttag gagtaatgtc                                    1110

<210> SEQ ID NO 2
<211> LENGTH: 370
<212> TYPE: PRT
<213> ORGANISM: Cricetulus griseus

<400> SEQUENCE: 2

Met Asn Val Lys Gly Lys Val Val Leu Ser Met Leu Val Val Ser Thr
1               5                   10                  15

Val Leu Val Val Phe Trp Glu Tyr Val Asn Ser Pro Glu Gly Ser Phe
            20                  25                  30

Leu Trp Ile Tyr His Met Lys Ile Pro Glu Ile Gly Asp Ser Ser Arg
        35                  40                  45
```

-continued

```
Gln Ser Trp Trp Phe Pro Ser Trp Phe Ser Asn Gly Thr His Ser Tyr
 50                  55                  60

Gln Glu Glu Asp Val Glu Arg Gly Arg Glu Lys Gln Arg Asn Ala Val
 65                  70                  75                  80

Arg Ile Glu Glu Pro His Leu Trp Asp Trp Phe Asn Pro Lys Asn Arg
                 85                  90                  95

Pro Glu Val Leu Thr Val Thr Pro Trp Lys Ala Pro Ile Val Trp Glu
            100                 105                 110

Gly Thr Tyr Asp Arg Ala Met Leu Glu Lys Tyr Tyr Ala Arg Gln Lys
        115                 120                 125

Ile Thr Val Gly Leu Thr Val Phe Ala Val Gly Lys Tyr Ile Glu His
130                 135                 140

Tyr Leu Glu Asp Phe Leu Glu Ser Ala Ser Arg Tyr Phe Met Val Gly
145                 150                 155                 160

His Arg Val Ile Phe Tyr Val Met Met Asp Asp Ala Ser Arg Met Pro
                165                 170                 175

Phe Ile His Leu Ser Pro Leu His Ser Leu Gln Val Phe Glu Ile Lys
            180                 185                 190

Ser Glu Thr Arg Trp Gln Asp Ile Ser Met Met Arg Met Lys Thr Ile
        195                 200                 205

Glu Glu His Ile Leu Thr His Ile Gln His Glu Val Asp Phe Leu Phe
210                 215                 220

Cys Met Asp Val Asp Gln Val Phe Gln Asp Asn Phe Gly Val Glu Thr
225                 230                 235                 240

Leu Gly Gln Leu Val Ala Gln Leu Gln Ala Trp Trp Tyr Lys Ala Asp
                245                 250                 255

His Asp Lys Phe Thr Tyr Glu Arg Arg Glu Leu Ser Ala Ala Tyr Ile
            260                 265                 270

Pro Phe Gly Gln Gly Asp Phe Tyr Tyr His Ala Ala Ile Phe Gly Gly
        275                 280                 285

Thr Pro Ile His Ile Leu Asn Leu Thr Arg Glu Cys Phe Glu Gly Ile
290                 295                 300

Leu Gln Asp Lys Asn Asn Asn Ile Glu Ala Lys Trp His Asp Glu Ser
305                 310                 315                 320

His Leu Asn Lys Tyr Phe Leu Phe Asn Lys Pro Thr Lys Ile Leu Ser
                325                 330                 335

Pro Glu Tyr Cys Trp Asp Tyr Gln Ile Gly Leu Pro Ser Glu Ile Lys
            340                 345                 350

Asn Val Lys Ile Ala Trp Gln Thr Lys Glu Tyr Asn Leu Val Arg Ser
        355                 360                 365

Asn Val
    370
```

<210> SEQ ID NO 3
<211> LENGTH: 1110
<212> TYPE: DNA
<213> ORGANISM: Cricetulus griseus

<400> SEQUENCE: 3

```
atgaatgtca agggaaaagt ggtcctgtcg atgctggttg tctcaactgt gcttgtcgtg      60
ttttgggaat atgtcaacag cccagaaggt tccttcttgt ggatatatca catgaaaatt     120
ccagagattg gtgacagcag caggcagagc tggtggttcc cgagctggtt tagcaatggg     180
acccacagtt atcaagaaga ggacatagaa gagggagag aaaagcagcg aaatgcagtc     240
agaattgaag agcctcactt gtgggactgg tttaatccaa agaaccgccc agaagttttg     300
```

```
acagtgaccc catggaaggc accaattgtg tgggaaggca cttatgacag agctatgctg    360
gaaaagtatt atgccagaca gaaaatcacc gtgggactga cagtttttgc tgtgggaaag    420
tacatcgagc attatttgga agatttccta gagtctgcta gcaggtactt catggttggc    480
cacagggtca tattttatgt catgatggac gatgcctcca gaatgccttt tatacacctg    540
agtcctctgc attccttaca agtgtttgag atcaagtctg agaccaggtg caagacatt     600 agcatgatgc gcatgaagac aatcgaggag cacatcctga cccacataca gcatgaggtc    660
gacttcctct tctgtatgga cgtggatcag gtctttcaag acaattttgg agtggagact    720
ctgggccagt tggtagctca gctccaggcc tggtggtaca aagctgacca cgacaagttt    780
acctatgaga ggcgggaact gtcggcggca tacatcccat ttggacaggg ggatttttat    840
taccatgcag ccatttttcgg agggacaccc attcatattc tcaacctcac ccggagtgc    900 tttgaggga tcctccagga caagaacaac aacatagaag caaagtggca tgacgaaagt    960
cacctaaaca aatatttcct tttcaacaag cccactaaaa ttttatctcc agagtactgt   1020
tgggactatc agataggctt gccttcagaa attaaaaatg taaagatagc ttggcagaca   1080
aaagagtata atttggttag gagtaatgtc                                    1110
```

<210> SEQ ID NO 4  
<211> LENGTH: 370  
<212> TYPE: PRT  
<213> ORGANISM: Cricetulus griseus

<400> SEQUENCE: 4

```
Met Asn Val Lys Gly Lys Val Val Leu Ser Met Leu Val Val Ser Thr
1               5                   10                  15

Val Leu Val Val Phe Trp Glu Tyr Val Asn Ser Pro Glu Gly Ser Phe
            20                  25                  30

Leu Trp Ile Tyr His Met Lys Ile Pro Glu Ile Gly Asp Ser Ser Arg
        35                  40                  45

Gln Ser Trp Trp Phe Pro Ser Trp Phe Ser Asn Gly Thr His Ser Tyr
    50                  55                  60

Gln Glu Glu Asp Ile Glu Arg Gly Arg Glu Lys Gln Arg Asn Ala Val
65                  70                  75                  80

Arg Ile Glu Glu Pro His Leu Trp Asp Trp Phe Asn Pro Lys Asn Arg
                85                  90                  95

Pro Glu Val Leu Thr Val Thr Pro Trp Lys Ala Pro Ile Val Trp Glu
            100                 105                 110

Gly Thr Tyr Asp Arg Ala Met Leu Glu Lys Tyr Tyr Ala Arg Gln Lys
        115                 120                 125

Ile Thr Val Gly Leu Thr Val Phe Ala Val Gly Lys Tyr Ile Glu His
    130                 135                 140

Tyr Leu Glu Asp Phe Leu Glu Ser Ala Ser Arg Tyr Phe Met Val Gly
145                 150                 155                 160

His Arg Val Ile Phe Tyr Val Met Met Asp Asp Ala Ser Arg Met Pro
                165                 170                 175

Phe Ile His Leu Ser Pro Leu His Ser Leu Gln Val Phe Glu Ile Lys
            180                 185                 190

Ser Glu Thr Arg Trp Gln Asp Ile Ser Met Met Arg Met Lys Thr Ile
        195                 200                 205

Glu Glu His Ile Leu Thr His Ile Gln His Glu Val Asp Phe Leu Phe
    210                 215                 220

Cys Met Asp Val Asp Gln Val Phe Gln Asp Asn Phe Gly Val Glu Thr
```

```
              225                 230                 235                 240

Leu Gly Gln Leu Val Ala Gln Leu Gln Ala Trp Trp Tyr Lys Ala Asp
                245                 250                 255

His Asp Lys Phe Thr Tyr Glu Arg Arg Glu Leu Ser Ala Ala Tyr Ile
                260                 265                 270

Pro Phe Gly Gln Gly Asp Phe Tyr Tyr His Ala Ala Ile Phe Gly Gly
                275                 280                 285

Thr Pro Ile His Ile Leu Asn Leu Thr Arg Glu Cys Phe Glu Gly Ile
            290                 295                 300

Leu Gln Asp Lys Asn Asn Asn Ile Glu Ala Lys Trp His Asp Glu Ser
305                 310                 315                 320

His Leu Asn Lys Tyr Phe Leu Phe Asn Lys Pro Thr Lys Ile Leu Ser
                325                 330                 335

Pro Glu Tyr Cys Trp Asp Tyr Gln Ile Gly Leu Pro Ser Glu Ile Lys
                340                 345                 350

Asn Val Lys Ile Ala Trp Gln Thr Lys Glu Tyr Asn Leu Val Arg Ser
                355                 360                 365

Asn Val
    370

<210> SEQ ID NO 5
<211> LENGTH: 5877
<212> TYPE: DNA
<213> ORGANISM: Cricetulus griseus

<400> SEQUENCE: 5
gaaccgccca gaagttttga cagtgacccc atggaaggcg ccaattgtgt gggaaggcac      60
ttatgacaga gctctgctgg aaaagtatta tgccagacag aaaatcaccg tggggctgac     120 ggttttgct gtgggaaagt aagcaaaaat gacaaacttg cccttgattt ttttttttctt     180 gttttaccat caaagtcatt gtgagggacc cgtagcccta cagaagcctc ccttactttg     240
agttactagg aaggagactt ccatttcctt tctgatgaca gctgaggagc aaaatcaata     300
gtaggtaagt ccacccattc ccaccacaga acggagagaa ctgtcttcag tgccaccgga     360
acccagagct aagagcatgc ctgccgctcc ctcctccctg acctctaggg ctttcctagg     420
gaggccccaa atgccagctg ttaatgccca ggaccaagga cggggttaga agttgtggag     480
tgtgctctgt gctccatggt ttccaggctg acatgtggct gctgctctct catgggcccc     540
tctggtcctg tctactggac cttcccggag gatttgaccc tggtgttgga tgatcagaac     600
ctgctgagcc tggacaggtt ctggctgcag cagcttccac ttccttattt agagctggat     660
gcagaaacat tgtactcatt cttgaagcta tgccattggt tttagtctaa cccattttgt     720
tttcttagtg cattaaccat tttcccctaa actaaaacat taggtttata ttttcattct     780
tttttccctt tctttctttc tttctttctt tctttctttc tttcttttct tgaggcagag     840
ttgcattttt aaggatgttt taagaaagga aaagtcagga ttatgagaga gccaccaaca     900
aagtaagaca tattggagag tgtgtgagtg taggcttctc tgagagaatc accctctgct     960
taaaaaaaaa aaaaaaaagt tttgtatcta gtgtgtgtgt gtaggtcaga ggatgacttt    1020
caggagttgg ctctcttctt ctactatgtg ggttctgggg atccaactta agtcttcagg    1080
cttggcagca agtgccctta catactgaga attcttgctg ttatgtttct ttttctgccc    1140
tctgagcctc tgtgttggaa cctcttatga aaaagtgaca aaatcaacag gatgttgact    1200 ccctgccat gttcaaaagg agtagaaggg gcagttggc ctgaccttga tctttgacaa      1260
gaacctaaaa gacagcaccg tgatgatgcc acagggcccc cacagcgccc agtgctgtct    1320
```

```
ttgggaaatt ttagcattgc tcagtgtgct gagtccctgg ggtccaatgg catcccaatg    1380
ggaaacagtg gctgtggagt tggacatttt cactagaaga atttgtattt tttagggtgg    1440
gattcaaggc tcaacttagc aaacactttt ggcacagaag ggaaagacag ctatattaca    1500
cattgatttg atccccaaag aacaaaatga acccactgtc tcacaatggc tatcaaccat    1560
ccaattacaa ctttgcagga aaatagaaaa caaacaata aaaaaaagtc ctacgactgc    1620
ctcccacttc ctggtgaaag ccgtgctccc agctaggcca gtctgcagtg gtgaatccca    1680
gaggaaatgc acctggacct ccgggaggtg tgacttttgc tttgcttttt atctcagtgc    1740
ctggagtcaa ctgtgatacc ttaacctctt aaacatcctc agatgtcaca gtgacactgc    1800
cctacactcc cctaagcatt gtttccccga acttcaggca cactagtttt tcttgaagtt    1860
cagagtacag aagtctgtct tgacctccag ccatggagtc atgtcagagc tctcttttac    1920
cactgggata tatttgcccc acccaaagaa tcagtactag aaaccttgag ctttgcaatg    1980
ccaacagtaa aagtgaaatt tatttcgatg gcaaagaaca acccaagcat caagaaaaac    2040
aaaacagaga ttggagagat ggctcagtgg ttgatagtat tggctgccct tctagtggac    2100
ccagggttca attcccagca ctcacatggt gtgaggaaaa agggcagcca agaaacaca    2160 cttggtccct ggaatcagac ccagagaaag aaatacatcc tggccctaaa attagagcca    2220
aaagactaaa aaggaccagt gaaagaaaca tactttggcc ctgaaaccag agccaaatct    2280
gaccctaatc ctgtgcagaa aaccaaccaa tccctgagca ggagatttag ccattcagag    2340
ctcagggatt gaaatctggc caatccccac cctggaaatc tccctggaaa aactccccta    2400
agattcccca tataaaccct gtatctgttc agcttgtggc tgcctggatt cttccctccc    2460
aataaatctc ttcaatgatg tttgaggtga gaccttcttt caccagagag cagatcggag    2520
tagggctgta acactttgct gctctccttg ccgaactgta acaactttac cagggaagcc    2580
ctctcctgca ggagcagagc tgatacactg ggaagccgtt ccctgaagca gggctgtaag    2640
ctgctatgct tactgtgacc tgtggtattc cttggctcct gattgccaga ataccttttcc    2700 atctgagctg taacactcag tattcttcgg ctttcaagtg ccgtaatcca tcccatccga    2760
tctgtcaaaa tgcttacaca tggcagctca caactgtctg taactccagt tccagggat     2820 ctggcaactt cacacaggca tacacacaag caaaacacaa atgcacataa aaataaatta    2880
ttggaaaaaa aagagaaaat gcaagtattt tttaaaaaag aaaaaaacac tagtcattct    2940
gcttggctag ttgtgtgctc agtaaactgt ggtccgtagt ctctgtgtgt aagtttgagg    3000
tttggaaagg gaccatctga cttcccctc atctctgcag tctccttggc atgaattagg     3060
aaaatagtct gtagcttgag cttgtataag gcatcagtat aatgtcactc aaatgataaa    3120
tagacaaatt gacaaatctc atctgttaga atggcaaaaa aaaaaaaaaa aaactgccaa    3180
taccaaatgt tgaaaaggtg tgaagtaatc agaatccttg tttactgcta gtgggaatat    3240
aatatggtac agccatcttg ggagaaattt tggcagttgc ttgcaaaatt gagcatgctc    3300
ttatcataat ctaatcatca aattccttgg tattaaccca agtgagttga aaaagtctta    3360
cacaaaaacc tgcatataga tattcttaaa agctttattc ataattgcta aaacttggga    3420
gcagacaagt tttcctttga caggcaaatg taaaaaatga attgtggtcc attcagataa    3480
cagaatatta ttcattctgc taaaagtga gctatgaagc catagaaagc aaggagaaat    3540
ttttgtcact aagtgaagaa cctaatctgg gaaggttcct atgctgtcag tattatatca    3600
ccttgtcaca gctggaggca ccagagagga ggagcctcag atcaggctgc agggcatttt    3660
ctaatgacta attgatggag gagagcccag cccattgtgg gtggagctat ccctgggctg    3720
```

```
gtggtcctgt attctataag aaagcagact aagacatgag ggacaagcca taagcagcac      3780
acctccatgg cttctgcatc agcttctgcc tccaggttcc taccctgttt gagttcctgt      3840
catgtcactt cagtgggtta ctatgtgaat gtgtgagcca ataatttttc cttctgaact      3900
tgcttttggt gttggtgttc caccaagggc aacagtaacc ttatgacagg tccatactgc      3960
cctgctttgg attctgattc tggaagaggc aaaactatag tgttaggaac aagattattg      4020
actcaagagc tgggggagag aggaggagaa aagaagagcc tagaagattc ttagggtagt      4080
gaagctattc tgaatgatac cacagcggtg gatatgcctg gcattgtgct tttgcacatt      4140
tcccaaagtg aaccttagta gaaactatgt tgtcagtgga agtgacaact attacaaacc      4200
tgctgtctgg agcatggtgg tcctagtagg aaggttgttc atttgtctag gcaggaggca      4260
tttgggtact cccaaacttt cagctcagtt ttgctcagaa ttcaaaatac agaagtatta      4320
aaatatagcc agactgtagc ttagatggtt gactaagctt tgcagtggag ctctaggttt      4380
gatcccaggt accacaaaaa ctgcacgtgt tgtggcatgt ttgtaatcct agcaggagta      4440
tgagaagttg aaggtcattc ttggctgcat agtgagtttg aggctagcct gacatacatg      4500
ataacctgtc tcaaaaaaaa aagttaaatt aagagaatca gagactgttc cagtatttgg      4560
atggatttgt aacatcatta tttgtctgga tgatacactg gtgtttgagg taaccagtag      4620
gaggtttgta gaatggccag gcaatgtggg gatttccatc ttccaccatt ccctgcatca      4680
cagaggatga tgggacggtg ccggtgggag tcgatctcca tcctacacac cattcctcgt      4740
atcacaaagg agggtgggac agtgctatgc ttagacttaa caaaacacag agaagataag      4800
gttgttatga atgcccgctg gacatgggca gcatacttgc tttgcatttg gcctggcagt      4860
agcgacactg gcctcagggt attccagggc tacaccttct ttgatggcag gcttccaaat      4920
ttgagaacag agccttaccg tgaggcttac tgcaaagcgg gtagttgaaa acacatacct      4980
ctcaggctgg cctgcttcca agagcaggag gacagggcta tgcatgccca gttgttctta      5040
cagagttggc agtggcagaa gttattccac tttccctgag gactgggaaa ggaccagctg      5100
gtggagagga gccagggtgc tgaactagca tgtgtccccg taagggtact agtgatggtt      5160
aaacatgtcc ccctctgttt caggtacata gagcattatt tggaagattt tctggagtct      5220
gctaacaggt acttcatggt tggccacagg gtcatatttt atgtcatggt ggacgatgcc      5280
tccagaatgc cttctataca cctgagtcct ctgcattcct tacaagtgtt tgagatcaag      5340
tccgagaagc gatggcagga catcagcatg atgcggatga agaccatcgg ggagcacatc      5400
ctgtcccaca tacagcacga ggtcgacttc ctcttctgca tggacgtgga tcaggtcttt      5460
caagacaatt tcggtgtgga gactctgggc cagttggtag ctcagctcca ggcctggtgg      5520
tacaaggccg atcgtgacaa gtttacctat gagaggcgga aactgtcggc ggcgtacatc      5580
ccgtttgggc aggggatttt ttattaccac gcagccattt ttggaggaac acccattcac      5640
attctcaacc tcacccgaga gtgctttgag ggaatcctcc aggacaagag caatgacatc      5700
gaagcagagt ggcacgatga gagccacctc aacaaatact tccttttcaa caaacccact      5760
aaaatcttat ctccagaata ctgttgggac tatcagatag gcttgccttc agaaattaaa      5820
aatgtaaagg tagcctggca gacaaaagag tataatttgg ttaggagtaa tgtctga         5877
```

<210> SEQ ID NO 6
<211> LENGTH: 828
<212> TYPE: DNA
<213> ORGANISM: Cricetulus griseus

<400> SEQUENCE: 6

```
aaccgcccag aagttttgac agtgacccca tggaaggcgc caattgtgtg ggaaggcact      60
tatgacagag ctctgctgga aaagtattat gccagacaga aaatcaccgt ggggctgacg     120
gttttttgctg tgggaaagta catagagcat tatttgaag attttctgga gtctgctaac     180
aggtacttca tggttggcca cagggtcata ttttatgtca tggtggacga tgcctccaga     240
atgccttcta tacacctgag tcctctgcat tccttacaag tgtttgagat caagtccgag     300
aagcgatggc aggacatcag catgatgcgg atgaagacca tcggggagca catcctgtcc     360
cacatacagc acgaggtcga cttcctcttc tgcatggacg tggatcaggt ctttcaagac     420
aatttcggtg tggagactct gggccagttg gtagctcagc tccaggcctg gtggtacaag     480
gccgatcgtg acaagtttac ctatgagagg cggaaactgt cggcggcgta catcccgttt     540
gggcagggggg atttttatta ccacgcagcc attttttggag gaacacccat tcacattctc     600
aacctcaccc gagagtgctt tgagggaatc ctccaggaca agagcaatga catcgaagca     660
gagtggcacg atgagagcca cctcaacaaa tacttccttt tcaacaaacc cactaaaatc     720
ttatctccag aatactgttg ggactatcag ataggcttgc cttcagaaat taaaaatgta     780
aaggtagcct ggcagacaaa agagtataat ttggttagga gtaatgtc                  828
```

<210> SEQ ID NO 7
<211> LENGTH: 276
<212> TYPE: PRT
<213> ORGANISM: Cricetulus griseus

<400> SEQUENCE: 7

```
Asn Arg Pro Glu Val Leu Thr Val Thr Pro Trp Lys Ala Pro Ile Val
1               5                   10                  15
Trp Glu Gly Thr Tyr Asp Arg Ala Leu Leu Glu Lys Tyr Tyr Ala Arg
            20                  25                  30
Gln Lys Ile Thr Val Gly Leu Thr Val Phe Ala Val Gly Lys Tyr Ile
        35                  40                  45
Glu His Tyr Leu Glu Asp Phe Leu Glu Ser Ala Asn Arg Tyr Phe Met
    50                  55                  60
Val Gly His Arg Val Ile Phe Tyr Val Met Val Asp Asp Ala Ser Arg
65                  70                  75                  80
Met Pro Ser Ile His Leu Ser Pro Leu His Ser Leu Gln Val Phe Glu
                85                  90                  95
Ile Lys Ser Glu Lys Arg Trp Gln Asp Ile Ser Met Met Arg Met Lys
            100                 105                 110
Thr Ile Gly Glu His Ile Leu Ser His Ile Gln His Glu Val Asp Phe
        115                 120                 125
Leu Phe Cys Met Asp Val Asp Gln Val Phe Gln Asp Asn Phe Gly Val
    130                 135                 140
Glu Thr Leu Gly Gln Leu Val Ala Gln Leu Gln Ala Trp Trp Tyr Lys
145                 150                 155                 160
Ala Asp Arg Asp Lys Phe Thr Tyr Glu Arg Arg Lys Leu Ser Ala Ala
                165                 170                 175
Tyr Ile Pro Phe Gly Gln Gly Asp Phe Tyr Tyr His Ala Ala Ile Phe
            180                 185                 190
Gly Gly Thr Pro Ile His Ile Leu Asn Leu Thr Arg Glu Cys Phe Glu
        195                 200                 205
Gly Ile Leu Gln Asp Lys Ser Asn Asp Ile Glu Ala Glu Trp His Asp
    210                 215                 220
Glu Ser His Leu Asn Lys Tyr Phe Leu Phe Asn Lys Pro Thr Lys Ile
```

```
225                 230                 235                 240
Leu Ser Pro Glu Tyr Cys Trp Asp Tyr Gln Ile Gly Leu Pro Ser Glu
                245                 250                 255
Ile Lys Asn Val Lys Val Ala Trp Gln Thr Lys Glu Tyr Asn Leu Val
            260                 265                 270
Arg Ser Asn Val
        275

<210> SEQ ID NO 8
<211> LENGTH: 24
<212> TYPE: DNA
<213> ORGANISM: Artificial Sequence
<220> FEATURE:
<223> OTHER INFORMATION: Chemically synthesized Ggta primer

<400> SEQUENCE: 8
tggatcacag gagaaaataa tgaa                                          24

<210> SEQ ID NO 9
<211> LENGTH: 27
<212> TYPE: DNA
<213> ORGANISM: Artificial Sequence
<220> FEATURE:
<223> OTHER INFORMATION: Chemically synthesized Ggta primer

<400> SEQUENCE: 9
aagtttccat cacaatttga agtcaga                                       27

<210> SEQ ID NO 10
<211> LENGTH: 28
<212> TYPE: DNA
<213> ORGANISM: Artificial Sequence
<220> FEATURE:
<223> OTHER INFORMATION: Chemically synthesized Ggta primer

<400> SEQUENCE: 10
gaaccgccca gaagttttga cagtgacc                                      28

<210> SEQ ID NO 11
<211> LENGTH: 29
<212> TYPE: DNA
<213> ORGANISM: Artificial Sequence
<220> FEATURE:
<223> OTHER INFORMATION: Chemically synthesized Ggta primer

<400> SEQUENCE: 11
gtcagacatt actcctaacc aaattatac                                     29

<210> SEQ ID NO 12
<211> LENGTH: 19
<212> TYPE: DNA
<213> ORGANISM: Artificial Sequence
<220> FEATURE:
<223> OTHER INFORMATION: Chemically synthesized Ggta primer

<400> SEQUENCE: 12
atgcctccag aatgccttt                                                19

<210> SEQ ID NO 13
<211> LENGTH: 20
<212> TYPE: DNA
<213> ORGANISM: Artificial Sequence
<220> FEATURE:
<223> OTHER INFORMATION: Chemically synthesized Ggta primer

<400> SEQUENCE: 13
```

-continued atccacgtcc atacagaaga    20

<210> SEQ ID NO 14
<211> LENGTH: 19
<212> TYPE: DNA
<213> ORGANISM: Artificial Sequence
<220> FEATURE:
<223> OTHER INFORMATION: Chemically synthesized Ggta primer

<400> SEQUENCE: 14
gccagacaga aaatcaccg    19

<210> SEQ ID NO 15
<211> LENGTH: 21
<212> TYPE: DNA
<213> ORGANISM: Artificial Sequence
<220> FEATURE:
<223> OTHER INFORMATION: Chemically synthesized Ggta primer

<400> SEQUENCE: 15
aaagacctga tccacgtcca t    21

<210> SEQ ID NO 16
<211> LENGTH: 20
<212> TYPE: DNA
<213> ORGANISM: Artificial Sequence
<220> FEATURE:
<223> OTHER INFORMATION: chemically synthesized Ggta primer

<400> SEQUENCE: 16
tgggaaggca cttatgacag    20

<210> SEQ ID NO 17
<211> LENGTH: 20
<212> TYPE: DNA
<213> ORGANISM: Artificial Sequence
<220> FEATURE:
<223> OTHER INFORMATION: Chemically synthesized Ggta primer

<400> SEQUENCE: 17
ttgtaaggaa tgcagaggac    20

<210> SEQ ID NO 18
<211> LENGTH: 19
<212> TYPE: DNA
<213> ORGANISM: Artificial Sequence
<220> FEATURE:
<223> OTHER INFORMATION: Chemically synthesized Ggta primer

<400> SEQUENCE: 18
gatgcctcca gaatgcctt    19

<210> SEQ ID NO 19
<211> LENGTH: 20
<212> TYPE: DNA
<213> ORGANISM: Artificial Sequence
<220> FEATURE:
<223> OTHER INFORMATION: Chemically synthesized Ggta primer

<400> SEQUENCE: 19
ctcattcttg aagctatgcc    20

<210> SEQ ID NO 20
<211> LENGTH: 19
<212> TYPE: DNA
<213> ORGANISM: Artificial Sequence

```
<220> FEATURE:
<223> OTHER INFORMATION: Chemically synthesized Ggta primer

<400> SEQUENCE: 20
gccagacaga aaatcaccg                                                19

<210> SEQ ID NO 21
<211> LENGTH: 19
<212> TYPE: DNA
<213> ORGANISM: Artificial Sequence
<220> FEATURE:
<223> OTHER INFORMATION: Chemically synthesized Ggta primer

<400> SEQUENCE: 21
cttacgggga cacatgcta                                                19

<210> SEQ ID NO 22
<211> LENGTH: 18
<212> TYPE: DNA
<213> ORGANISM: Artificial Sequence
<220> FEATURE:
<223> OTHER INFORMATION: Chemically synthesized Ggta primer

<400> SEQUENCE: 22
ggcacagaag ggaaagac                                                 18

<210> SEQ ID NO 23
<211> LENGTH: 21
<212> TYPE: DNA
<213> ORGANISM: Artificial Sequence
<220> FEATURE:
<223> OTHER INFORMATION: Chemically synthesized Ggta primer

<400> SEQUENCE: 23
gtcaaccatc taagctacag t                                             21

<210> SEQ ID NO 24
<211> LENGTH: 21
<212> TYPE: DNA
<213> ORGANISM: Artificial Sequence
<220> FEATURE:
<223> OTHER INFORMATION: Chemically synthesized Ggta primer

<400> SEQUENCE: 24
aaatctgacc ctaatcctgt g                                             21

<210> SEQ ID NO 25
<211> LENGTH: 20
<212> TYPE: DNA
<213> ORGANISM: Artificial Sequence
<220> FEATURE:
<223> OTHER INFORMATION: Chemically synthesized Ggta primer

<400> SEQUENCE: 25
ctccttgctt tctatggctt                                               20

<210> SEQ ID NO 26
<211> LENGTH: 18
<212> TYPE: DNA
<213> ORGANISM: Artificial Sequence
<220> FEATURE:
<223> OTHER INFORMATION: Chemically synthesized Ggta primer

<400> SEQUENCE: 26
gccagacaga aaatcacc                                                 18
```

```
<210> SEQ ID NO 27
<211> LENGTH: 22
<212> TYPE: DNA
<213> ORGANISM: Artificial Sequence
<220> FEATURE:
<223> OTHER INFORMATION: Chemically synthesized Ggta primer

<400> SEQUENCE: 27
gtctccttcc tagtaactca aa                                              22

<210> SEQ ID NO 28
<211> LENGTH: 19
<212> TYPE: DNA
<213> ORGANISM: Artificial Sequence
<220> FEATURE:
<223> OTHER INFORMATION: Chemically synthesized Ggta primer

<400> SEQUENCE: 28
ctagcatgtg tccccgtaa                                                  19

<210> SEQ ID NO 29
<211> LENGTH: 16
<212> TYPE: DNA
<213> ORGANISM: Artificial Sequence
<220> FEATURE:
<223> OTHER INFORMATION: Chemically synthesized Ggta primer

<400> SEQUENCE: 29
gctggtggtt cccgag                                                     16

<210> SEQ ID NO 30
<211> LENGTH: 21
<212> TYPE: DNA
<213> ORGANISM: Artificial Sequence
<220> FEATURE:
<223> OTHER INFORMATION: Chemically synthesized Ggta primer

<400> SEQUENCE: 30
aaagacctga tccacgtcca t                                               21

<210> SEQ ID NO 31
<211> LENGTH: 20
<212> TYPE: DNA
<213> ORGANISM: Artificial Sequence
<220> FEATURE:
<223> OTHER INFORMATION: Chemically synthesized Ggta primer

<400> SEQUENCE: 31
gaagttttga cagtgacccc                                                 20

<210> SEQ ID NO 32
<211> LENGTH: 23
<212> TYPE: DNA
<213> ORGANISM: Artificial Sequence
<220> FEATURE:
<223> OTHER INFORMATION: Chemically synthesized Ggta primer

<400> SEQUENCE: 32
gtttttgctg tgggaaagta cat                                             23

<210> SEQ ID NO 33
<211> LENGTH: 20
<212> TYPE: DNA
<213> ORGANISM: Artificial Sequence
<220> FEATURE:
<223> OTHER INFORMATION: Chemically synthesized Ggta primer

<400> SEQUENCE: 33
```
ttgtaaggaa tgcagaggac                                              20

<210> SEQ ID NO 34
<211> LENGTH: 20
<212> TYPE: DNA
<213> ORGANISM: Artificial Sequence
<220> FEATURE:
<223> OTHER INFORMATION: Chemically synthesized Ggta primer

<400> SEQUENCE: 34
aaagacctga tccacgtcca                                              20

<210> SEQ ID NO 35
<211> LENGTH: 24
<212> TYPE: DNA
<213> ORGANISM: Artificial Sequence
<220> FEATURE:
<223> OTHER INFORMATION: Chemically synthesized Ggta primer

<400> SEQUENCE: 35
gatctcaaac acttgtaagg aatg                                         24

<210> SEQ ID NO 36
<211> LENGTH: 20
<212> TYPE: DNA
<213> ORGANISM: Artificial Sequence
<220> FEATURE:
<223> OTHER INFORMATION: Chemically synthesized Ggta primer

<400> SEQUENCE: 36
tgggaaggca cttatgacag                                              20

<210> SEQ ID NO 37
<211> LENGTH: 23
<212> TYPE: DNA
<213> ORGANISM: Artificial Sequence
<220> FEATURE:
<223> OTHER INFORMATION: Chemically synthesized Ggta primer

<400> SEQUENCE: 37
aaattccaga gattggtgac agc                                          23

<210> SEQ ID NO 38
<211> LENGTH: 21
<212> TYPE: DNA
<213> ORGANISM: Artificial Sequence
<220> FEATURE:
<223> OTHER INFORMATION: Chemically synthesized Ggta primer

<400> SEQUENCE: 38
gtcataagtg ccttcccaca c                                            21

<210> SEQ ID NO 39
<211> LENGTH: 20
<212> TYPE: DNA
<213> ORGANISM: Artificial Sequence
<220> FEATURE:
<223> OTHER INFORMATION: Chemically synthesized Ggta primer

<400> SEQUENCE: 39
ttattaccac gcagccattt                                              20

<210> SEQ ID NO 40
<211> LENGTH: 23
<212> TYPE: DNA
<213> ORGANISM: Artificial Sequence

```
<220> FEATURE:
<223> OTHER INFORMATION: Chemically synthesized Ggta primer

<400> SEQUENCE: 40
ttccatcaca atttgaagtc aga                                          23

<210> SEQ ID NO 41
<211> LENGTH: 29
<212> TYPE: DNA
<213> ORGANISM: Artificial Sequence
<220> FEATURE:
<223> OTHER INFORMATION: Chemically synthesized Ggta primer

<400> SEQUENCE: 41
gtcagacatt actcctaacc aaattatac                                    29

<210> SEQ ID NO 42
<211> LENGTH: 25
<212> TYPE: DNA
<213> ORGANISM: Artificial Sequence
<220> FEATURE:
<223> OTHER INFORMATION: Chemically synthesized Ggta primer

<400> SEQUENCE: 42
aatgaatgtc aagggaaaag tggtc                                        25

<210> SEQ ID NO 43
<211> LENGTH: 21
<212> TYPE: DNA
<213> ORGANISM: Artificial Sequence
<220> FEATURE:
<223> OTHER INFORMATION: Chemically synthesized Ggta primer

<400> SEQUENCE: 43
tgatagtccc aacagtactc t                                            21

<210> SEQ ID NO 44
<211> LENGTH: 20
<212> TYPE: DNA
<213> ORGANISM: Artificial Sequence
<220> FEATURE:
<223> OTHER INFORMATION: Chemically synthesized Ggta primer

<400> SEQUENCE: 44
cacatcctga cccacataca                                              20

<210> SEQ ID NO 45
<211> LENGTH: 20
<212> TYPE: DNA
<213> ORGANISM: Artificial Sequence
<220> FEATURE:
<223> OTHER INFORMATION: Chemically synthesized Ggta primer

<400> SEQUENCE: 45
gacagttccc gcctctcata                                              20

<210> SEQ ID NO 46
<211> LENGTH: 19
<212> TYPE: DNA
<213> ORGANISM: Artificial Sequence
<220> FEATURE:
<223> OTHER INFORMATION: Chemically synthesized Ggta primer

<400> SEQUENCE: 46
atgcctccag aatgccttt                                               19
```

<210> SEQ ID NO 47
<211> LENGTH: 20
<212> TYPE: DNA
<213> ORGANISM: Artificial Sequence
<220> FEATURE:
<223> OTHER INFORMATION: Chemically synthesized Ggta primer

<400> SEQUENCE: 47
atccacgtcc atacagaaga                                              20

<210> SEQ ID NO 48
<211> LENGTH: 23
<212> TYPE: DNA
<213> ORGANISM: Artificial Sequence
<220> FEATURE:
<223> OTHER INFORMATION: Chemically synthesized Ggta primer

<400> SEQUENCE: 48
gtacattgag cattatttgg aag                                          23

<210> SEQ ID NO 49
<211> LENGTH: 23
<212> TYPE: DNA
<213> ORGANISM: Artificial Sequence
<220> FEATURE:
<223> OTHER INFORMATION: Chemically synthesized Ggta primer

<400> SEQUENCE: 49
gtacatcgag cattatttgg aag                                          23

<210> SEQ ID NO 50
<211> LENGTH: 28
<212> TYPE: DNA
<213> ORGANISM: Artificial Sequence
<220> FEATURE:
<223> OTHER INFORMATION: Chemically synthesized Ggta primer

<400> SEQUENCE: 50
gaaccgccca gaagttttga cagtgacc                                     28

<210> SEQ ID NO 51
<211> LENGTH: 16
<212> TYPE: DNA
<213> ORGANISM: Artificial Sequence
<220> FEATURE:
<223> OTHER INFORMATION: Chemically synthesized Ggta primer

<400> SEQUENCE: 51
gctggtggtt cccgag                                                  16

<210> SEQ ID NO 52
<211> LENGTH: 22
<212> TYPE: DNA
<213> ORGANISM: Artificial Sequence
<220> FEATURE:
<223> OTHER INFORMATION: Chemically synthesized Ggta primer

<400> SEQUENCE: 52
gtctccttcc tagtaactca aa                                           22

<210> SEQ ID NO 53
<211> LENGTH: 23
<212> TYPE: DNA
<213> ORGANISM: Artificial Sequence
<220> FEATURE:
<223> OTHER INFORMATION: Chemically synthesized Ggta primer -continued

```
<400> SEQUENCE: 53
atgaaaattc cagagattgg tga                                            23

<210> SEQ ID NO 54
<211> LENGTH: 22
<212> TYPE: DNA
<213> ORGANISM: Artificial Sequence
<220> FEATURE:
<223> OTHER INFORMATION: Chemically synthesized Ggta primer

<400> SEQUENCE: 54
gggcacccac agttatcaag aa                                             22

<210> SEQ ID NO 55
<211> LENGTH: 23
<212> TYPE: DNA
<213> ORGANISM: Artificial Sequence
<220> FEATURE:
<223> OTHER INFORMATION: Chemically synthesized Ggta primer

<400> SEQUENCE: 55
gtcagaattg aggagcctca ctt                                            23

<210> SEQ ID NO 56
<211> LENGTH: 368
<212> TYPE: PRT
<213> ORGANISM: Bos taurus

<400> SEQUENCE: 56
```

Met Asn Val Lys Gly Lys Val Ile Leu Ser Met Leu Val Val Ser Thr
1               5                   10                  15

Val Ile Val Val Phe Trp Glu Tyr Ile His Ser Pro Glu Gly Ser Leu
            20                  25                  30

Phe Trp Ile Asn Pro Ser Arg Asn Pro Glu Val Gly Gly Ser Ser Ile
        35                  40                  45

Gln Lys Gly Trp Trp Leu Pro Arg Trp Phe Asn Asn Gly Tyr His Glu
    50                  55                  60

Glu Asp Gly Asp Ile Asn Glu Glu Lys Glu Gln Arg Asn Glu Asp Glu
65                  70                  75                  80

Ser Lys Leu Lys Leu Ser Asp Trp Phe Asn Pro Phe Lys Arg Pro Glu
                85                  90                  95

Val Val Thr Met Thr Lys Trp Lys Ala Pro Val Val Trp Glu Gly Thr
            100                 105                 110

Tyr Asn Arg Ala Val Leu Asp Asn Tyr Tyr Ala Lys Gln Lys Ile Thr
        115                 120                 125

Val Gly Leu Thr Val Phe Ala Val Gly Arg Tyr Ile Glu His Tyr Leu
    130                 135                 140

Glu Glu Phe Leu Thr Ser Ala Asn Lys His Phe Met Val Gly His Pro
145                 150                 155                 160

Val Ile Phe Tyr Ile Met Val Asp Asp Val Ser Arg Met Pro Leu Ile
                165                 170                 175

Glu Leu Gly Pro Leu Arg Ser Phe Lys Val Phe Lys Ile Lys Pro Glu
            180                 185                 190

Lys Arg Trp Gln Asp Ile Ser Met Met Arg Met Lys Thr Ile Gly Glu
        195                 200                 205

His Ile Val Ala His Ile Gln His Glu Val Asp Phe Leu Phe Cys Met
    210                 215                 220

Asp Val Asp Gln Val Phe Gln Asp Lys Phe Gly Val Glu Thr Leu Gly
225                 230                 235                 240

```
Glu Ser Val Ala Gln Leu Gln Ala Trp Trp Tyr Lys Ala Asp Pro Asn
            245                 250                 255

Asp Phe Thr Tyr Glu Arg Arg Lys Glu Ser Ala Ala Tyr Ile Pro Phe
        260                 265                 270

Gly Glu Gly Asp Phe Tyr Tyr His Ala Ala Ile Phe Gly Gly Thr Pro
    275                 280                 285

Thr Gln Val Leu Asn Ile Thr Gln Glu Cys Phe Lys Gly Ile Leu Lys
    290                 295                 300

Asp Lys Lys Asn Asp Ile Glu Ala Gln Trp His Asp Glu Ser His Leu
305                 310                 315                 320

Asn Lys Tyr Phe Leu Leu Asn Lys Pro Thr Lys Ile Leu Ser Pro Glu
                325                 330                 335

Tyr Cys Trp Asp Tyr His Ile Gly Leu Pro Ala Asp Ile Lys Leu Val
            340                 345                 350

Lys Met Ser Trp Gln Thr Lys Glu Tyr Asn Val Val Arg Asn Asn Val
            355                 360                 365

<210> SEQ ID NO 57
<211> LENGTH: 370
<212> TYPE: PRT
<213> ORGANISM: Canis familiaris

<400> SEQUENCE: 57

Met Asn Val Lys Gly Lys Val Ile Leu Ser Met Leu Val Val Ser Thr
1               5                   10                  15

Val Ile Val Val Phe Trp Glu Tyr Ile Asn Ser Pro Glu Gly Ser Phe
            20                  25                  30

Leu Trp Ile Tyr His Ser Lys Asn Pro Glu Val Gly Glu Ser Arg Ile
        35                  40                  45

Gln Lys Gly Trp Trp Phe Pro Asn Trp Phe Asn Asn Gly Thr His Phe
    50                  55                  60

Tyr Gln Glu Glu Glu Asp Ile Asp Asp Glu Asn Glu Gln Gly Glu Glu
65                  70                  75                  80

Asn Asn Ala Glu Leu Gln Leu Ser Asp Trp Phe Asn Pro Gln Lys Arg
                85                  90                  95

Pro Glu Val Val Thr Val Thr Arg Trp Lys Ala Pro Val Val Trp Glu
            100                 105                 110

Gly Thr Tyr Asn Ser Thr Ile Leu Glu Asn Tyr Tyr Ala Lys Gln Lys
        115                 120                 125

Ile Thr Ile Gly Leu Thr Val Phe Ala Val Gly Arg Tyr Ile Glu His
    130                 135                 140

Tyr Leu Glu Glu Phe Leu Ile Ser Ala Asn Arg Tyr Phe Met Val Gly
145                 150                 155                 160

His Lys Val Ile Phe Tyr Ile Met Val Asp Asp Val Ser Arg Met Pro
                165                 170                 175

Leu Val Glu Leu Gly Pro Leu Arg Ser Phe Lys Val Phe Glu Ile Glu
            180                 185                 190

Pro Glu Lys Arg Trp Gln Asp Ile Ser Met Met Arg Met Lys Thr Ile
        195                 200                 205

Gly Glu His Ile Val Ala His Ile Gln His Glu Val Asp Phe Leu Phe
    210                 215                 220

Cys Met Asp Val Asp Gln Val Phe Gln Asp Ser Phe Gly Val Glu Thr
225                 230                 235                 240

Leu Gly Gln Ser Val Ala Gln Leu Gln Ala Trp Trp Tyr Lys Ala Asp
                245                 250                 255
```

```
Pro Asp Glu Phe Thr Tyr Glu Arg Arg Lys Glu Ser Ala Ala Tyr Ile
            260                 265                 270

Pro Phe Gly Gln Gly Asp Phe Tyr His Ala Ala Ile Phe Gly Gly
            275                 280                 285

Thr Pro Ile Gln Val Leu Asn Ile Thr Gln Glu Cys Phe Lys Gly Ile
            290                 295                 300

Leu Gln Asp Lys Lys Asn Asp Ile Glu Ala Glu Trp His Asp Glu Ser
305                 310                 315                 320

His Leu Asn Lys Tyr Phe Leu Leu Asn Lys Pro Thr Lys Ile Leu Ser
                325                 330                 335

Pro Glu Tyr Cys Trp Asp Tyr His Ile Gly Leu Pro Ser Asp Ile Lys
            340                 345                 350

Thr Val Lys Ile Ser Trp Gln Thr Lys Glu Tyr Asn Leu Val Arg Asn
            355                 360                 365

Asn Ile
    370

<210> SEQ ID NO 58
<211> LENGTH: 337
<212> TYPE: PRT
<213> ORGANISM: Rattus norvegicus

<400> SEQUENCE: 58

Met Asn Val Lys Gly Lys Ile Ile Leu Ser Val Leu Met Val Ser Thr
1               5                   10                  15

Val Leu Val Val Phe Trp Glu Tyr Val Asn Arg Thr His Ser Tyr Gln
            20                  25                  30

Glu Glu Asp Ile Glu Arg Ala Arg Glu Lys Gly Arg Asn Gly Asp Ser
            35                  40                  45

Ile Val Glu Pro Gln Leu Trp Asp Trp Phe Asn Pro Lys Asn Arg Pro
50                  55                  60

Glu Val Leu Thr Val Thr Pro Trp Lys Ala Pro Ile Val Trp Glu Gly
65                  70                  75                  80

Thr Tyr Asp Thr Ala Leu Leu Glu Lys Tyr Tyr Ala Arg Gln Lys Ile
                85                  90                  95

Thr Val Gly Leu Thr Val Phe Ala Val Gly Lys Tyr Ile Glu His Tyr
            100                 105                 110

Leu Glu Asp Phe Leu Glu Ser Ala Asn Lys Tyr Phe Met Val Gly His
            115                 120                 125

Arg Val Ile Phe Tyr Val Met Met Asp Asp Thr Ser Arg Met Pro Ala
130                 135                 140

Val His Leu Ser Pro Leu His Ser Leu Gln Val Phe Glu Ile Arg Ser
145                 150                 155                 160

Glu Lys Arg Trp Gln Asp Ile Ser Met Met Arg Met Lys Thr Ile Gly
                165                 170                 175

Glu His Ile Leu Asp His Ile Gln His Glu Val Asp Phe Leu Phe Cys
            180                 185                 190

Met Asp Val Asp Gln Val Phe Gln Asp Asn Phe Gly Val Glu Thr Leu
            195                 200                 205

Gly Gln Leu Val Ala Gln Leu Gln Ala Trp Trp Tyr Lys Ala Ser Pro
210                 215                 220

Asp Glu Phe Thr Tyr Glu Arg Arg Glu Leu Ser Ala Ala Tyr Ile Pro
225                 230                 235                 240

Phe Gly Glu Gly Asp Phe Tyr Tyr His Ala Ala Val Phe Gly Gly Thr
                245                 250                 255
```

```
Pro Val His Ile Leu Asn Leu Thr Arg Glu Cys Phe Lys Gly Ile Leu
            260                 265                 270

Gln Asp Lys Lys His Asp Ile Glu Ala Gln Trp His Asp Glu Ser His
        275                 280                 285

Leu Asn Lys Tyr Phe Leu Phe Asn Lys Pro Thr Lys Ile Leu Ser Pro
    290                 295                 300

Glu Tyr Cys Trp Asp Tyr His Ile Gly Leu Pro Ser Asp Ile Lys Asn
305                 310                 315                 320

Val Lys Ile Ala Trp Gln Thr Lys Glu Tyr Asn Leu Val Arg Ser Asn
                325                 330                 335

Val

<210> SEQ ID NO 59
<211> LENGTH: 371
<212> TYPE: PRT
<213> ORGANISM: Mus musculus

<400> SEQUENCE: 59

Met Asn Val Lys Gly Lys Val Ile Leu Leu Met Leu Ile Val Ser Thr
1               5                   10                  15

Val Val Val Val Phe Trp Glu Tyr Val Asn Ser Pro Glu Gly Ser Phe
            20                  25                  30

Leu Trp Ile Tyr His Thr Lys Ile Pro Glu Val Gly Asn Arg Trp
        35                  40                  45

Gln Lys Asp Trp Trp Phe Pro Ser Trp Phe Lys Asn Gly Thr His Ser
    50                  55                  60

Tyr Gln Glu Asp Asn Val Glu Gly Arg Arg Glu Lys Gly Arg Asn Gly
65                  70                  75                  80

Asp Arg Ile Glu Glu Pro Gln Leu Trp Asp Trp Phe Asn Pro Lys Asn
                85                  90                  95

Arg Pro Asp Val Leu Thr Val Thr Pro Trp Lys Ala Pro Ile Val Trp
            100                 105                 110

Glu Gly Thr Tyr Asp Thr Ala Leu Leu Glu Lys Tyr Tyr Ala Thr Gln
        115                 120                 125

Lys Leu Thr Val Gly Leu Thr Val Phe Ala Val Gly Lys Tyr Ile Glu
    130                 135                 140

His Tyr Leu Glu Asp Phe Leu Glu Ser Ala Asp Met Tyr Phe Met Val
145                 150                 155                 160

Gly His Arg Val Ile Phe Tyr Val Met Ile Asp Asp Thr Ser Arg Met
                165                 170                 175

Pro Val Val His Leu Asn Pro Leu His Ser Leu Gln Val Phe Glu Ile
            180                 185                 190

Arg Ser Glu Lys Arg Trp Gln Asp Ile Ser Met Met Arg Met Lys Thr
        195                 200                 205

Ile Gly Glu His Ile Leu Ala His Ile Gln His Glu Val Asp Phe Leu
    210                 215                 220

Phe Cys Met Asp Val Asp Gln Val Phe Gln Asp Asn Phe Gly Val Glu
225                 230                 235                 240

Thr Leu Gly Gln Leu Val Ala Gln Leu Gln Ala Trp Trp Tyr Lys Ala
                245                 250                 255

Ser Pro Glu Lys Phe Thr Tyr Glu Arg Arg Glu Leu Ser Ala Ala Tyr
            260                 265                 270

Ile Pro Phe Gly Glu Gly Asp Phe Tyr Tyr His Ala Ala Ile Phe Gly
        275                 280                 285
```

-continued

```
Gly Thr Pro Thr His Ile Leu Asn Leu Thr Arg Glu Cys Phe Lys Gly
        290             295             300

Ile Leu Gln Asp Lys Lys His Asp Ile Glu Ala Gln Trp His Asp Glu
305             310             315             320

Ser His Leu Asn Lys Tyr Phe Leu Phe Asn Lys Pro Thr Lys Ile Leu
                325             330             335

Ser Pro Glu Tyr Cys Trp Asp Tyr Gln Ile Gly Leu Pro Ser Asp Ile
                340             345             350

Lys Ser Val Lys Val Ala Trp Gln Thr Lys Glu Tyr Asn Leu Val Arg
        355             360             365

Asn Asn Val
    370
```

GLYCOSYL TRANSFERASE FROM CHINESE HAMSTER AND RELATED METHODS

The present application claims priority to United States Provisional patent application Ser. No. 61/260,232, filed on Nov. 11, 2009, the entire disclosure of which is incorporated herein by reference.

In accordance with 37 CFR 1.52(e)(5), a Sequence Listing in the form of a text file (entitled "M0061 Sequence Listing.txt," created on Dec. 10, 2012, and 43 kilobytes) is incorporated herein by reference in its entirety.

BACKGROUND OF THE INVENTION

The terminal galactose-α1,3-galactose glycan (herein referred to as Gal-α-Gal) can be a functionally consequential modification to N-glycosylated proteins given its immunogenic potential in humans when presented on heterologously derived biologic therapeutics. The presence of this carbohydrate epitope on endogenous proteins appears to be highly species specific, e.g., detected in pig, mouse, and rat, but absent in primates. Thus, the epitope can be present on recombinant biologics produced in cellular expression systems derived from certain organisms (e.g., Mouse NS0 or SP/2 cells, transgenic pigs). The monoclonal antibody cetuximab (Erbitux®) is one such example of a commercial protein drug product produced in a mouse derived cell line and also reported to contain the Gal-α-Gal carbohydrate epitope (Chung et al. (2008) *N Engl J Med* 358:1109-1117). The enzymatic biosynthesis of the Gal-α1,3-Gal glycan has been ascribed to 1,3 glycosyl transferase-1 (herein referred to as Ggta1) (Taylor et al. (2003) *Glycobiology* 13:327-337; Smith et al. (1990) *J Biol Chem* 265:6225-6234).

SUMMARY OF THE INVENTION

The invention is based, at least in part, on the discovery of α-1,3 glycosyl transferase-1 (Ggat1) gene sequences in both the Chinese Hamster (*Cricetulus griseus*) from which CHO cells are derived and in a CHO cell line used for recombinant protein production. Accordingly, the invention relates to nucleic acid and polypeptide compositions related to the discovered genes, and related vectors and cells (e.g., CHO cells genetically engineered to reduce, eliminate or increase Ggta1 activity and vectors useful for producing such cells). In addition, the invention relates to the use of the identified sequences in various methods, e.g., methods to detect Ggta1 activity in CHO cells (including Ggta1 transcriptional activity and/or enzymatic activity), e.g., for screening CHO cells for the ability to produce Gal-α-Gal structures, or to identify and quantify Ggta1 expression or activity in a CHO cell, e.g., a cell used for production of a therapeutic glycoprotein.

The Ggta1 sequences disclosed herein are listed in Table 1:

TABLE 1

| SOURCE (NAME) | TYPE OF SEQUENCE | SEQ ID NO |
|---|---|---|
| Chinese hamster ovary tissue (Ggta1-a) | DNA; full length coding sequence (FIG. 3) | SEQ ID NO: 1 |
| Chinese hamster ovary tissue (Ggta1-a) | polypeptide; translated full length coding sequence (FIG. 3) | SEQ ID NO: 2 |
| Chinese hamster spleen tissue (Ggta1-b) | DNA; full length coding sequence (FIG. 4) | SEQ ID NO: 3 |
| Chinese hamster spleen tissue (Ggta1-b) | polypeptide; translated full length coding sequence (FIG. 4) | SEQ ID NO: 4 |
| Chinese hamster ovary (CHO) cell line (Ggta1-c) | DNA; genomic DNA sequence corresponding to exons 8 and 9 and intervening intron (FIG. 5) | SEQ ID NO: 5 |
| Chinese hamster ovary (CHO) cell line (Ggta1-c) | DNA; coding sequence of exons 8 and 9 (FIG. 6) | SEQ ID NO: 6 |
| Chinese hamster ovary (CHO) cell line (Ggta1-c) | polypeptide; translated sequence of exons 8 and 9 (FIG. 6) | SEQ ID NO: 7 |

Accordingly, in a first aspect, the invention features an isolated nucleic acid molecule comprising a nucleotide sequence that encodes a Chinese hamster or CHO cell Ggta1 polypeptide, or an active portion thereof having one or more Ggta1 activity, e.g., a Ggta1 activity described herein.

In one embodiment, the isolated nucleic acid molecule comprises a nucleotide sequence having at least about 75% sequence identity, or at least about 80% sequence identity, or at least about 85% sequence identity, or at least about 90% sequence identity, or at least about 91% sequence identity, or at least about 92% sequence identity, or at least about 93% sequence identity, or at least about 94% sequence identity, or at least about 95% sequence identity, or at least about 96% sequence identity, or at least about 97% sequence identity, or at least about 98% sequence identity, or at least about 99% sequence identity to (a) a DNA molecule that has a sequence that encodes the sequence of amino acid residues of SEQ ID NO:2, or SEQ ID NO:4 or SEQ ID NO:7 or (b) the complement of the DNA molecule of (a). The isolated nucleic acid molecule can encode a polypeptide having one or more Ggta1 activity. In one embodiment, the isolated nucleic acid molecule encodes the sequence of SEQ ID NO:2, or SEQ ID NO:4 or SEQ ID NO:7.

In one embodiment, the isolated nucleic acid molecule has at least about 90% sequence identity, or at least about 91% sequence identity, or at least about 92% sequence identity, or at least about 93% sequence identity, or at least about 94% sequence identity, or at least about 95% sequence identity, or at least about 96% sequence identity, or at least about 97% sequence identity, or at least about 98% sequence identity, or at least about 99% sequence identity to the sequence of SEQ ID NO:1 or SEQ ID NO:3, SEQ ID NO:5 or SEQ ID NO:6. The isolated nucleic acid molecule can encode a polypeptide having one or more Ggta1 activity.

In one embodiment, the isolated nucleic acid molecule hybridizes under high stringency conditions to a nucleic acid molecule comprising the nucleotide sequence of SEQ ID NO:1, SEQ ID NO:3, SEQ ID NO:5 or SEQ ID NO:6.

In one embodiment, the isolated nucleic acid molecule comprises the nucleotide sequence of SEQ ID NO:1 or SEQ ID NO:3, SEQ ID NO:5 or SEQ ID NO:6.

An isolated nucleic acid molecule of the invention may correspond to a naturally-occurring nucleic acid molecule, e.g., to a naturally occurring CHO nucleic acid sequence that encodes an expressed Ggta1 protein. In some embodiments, the nucleic acid molecule can encode a polypeptide that has one or more Ggta1 activity, whether or not the nucleic acid molecule is naturally-occurring. For example, the isolated nucleic acid molecule is a non-naturally occurring variant of a Chinese hamster or CHO cell Ggta1 sequence. In one embodiment, the isolated nucleic acid molecule is an antisense nucleic acid molecule, an RNAi molecule (e.g., a dsRNA or siRNA), a ribozyme, or a peptide nucleic acid, wherein the antisense molecule inhibits the production of Ggta1 described herein.

In one embodiment, the isolated nucleic acid molecule encodes a Ggta1 polypeptide described herein linked to a heterologous amino acid sequence, e.g., it encodes a Ggta1 fusion protein, e.g., an epitope-tagged Ggta1.

In a second aspect, the invention features an oligonucleotide comprising at least 10 consecutive nucleotides (e.g., at least 12, 15, 18, 20, 25, 30, 35, 40, 45 or 50 consecutive nucleotides) and less than 500 consecutive nucleotides (e.g., less that 450, 400, 350, 300, 250, 200, 180, 160, 140, 130, 125, 120, 100, 90, 80, 75, 60, or 50 consecutive nucleotides) of SEQ ID NO:1 or its complement, SEQ ID NO:3 or its complement, SEQ ID NO:5 or its complement, or SEQ ID NO:6 or its complement. In one embodiment, the oligonucleotide is between 10 and 200 nucleotides in length, between 20 and 200 nucleotides in length, between 20 and 100 nucleotides in length, between 15 and 100 nucleotides in length, between 10 and 100 nucleotides in length, between 20 and 75 nucleotides in length, between 25 and 50 nucleotides in length, between 20 and 50 nucleotides in length, between 15 and 50 nucleotides in length, between 10 and 50 nucleotides in length, between 10 and 40 nucleotides in length, between 10 and 30 nucleotides in length, or between 10 and 25 nucleotides in length. Such oligonucleotides can be used, e.g., as primers, tags or probes in methods to detect and/or measure the expression of Ggta1 in CHO cells (e.g., using methods such as PCR, DNA chips, or serial analysis of gene expression (SAGE)). In one embodiment, the oligonucleotide has or includes a sequence shown in Table 2 or Table 4.

In one embodiment, the oligonucleotide has one or more of the following characteristics: GC content of 50-65%, lack of substantial secondary structure, melting point (Tm) between 50 and 60° C., no GC repeats longer than 3 bases, GC pairs at the ends, spans an intron-exon border.

In one embodiment, the invention features a set of two such oligonucleotides (e.g., a primer pair) that are capable together of amplifying at least a portion of a Ggta1 DNA derived from CHO cells, e.g., by PCR. One exemplary set of primers includes a forward primer that anneals to the coding strand of a Ggta1 nucleic acid molecule and a reverse primer that anneals to the non-coding strand of a Ggta1 nucleic acid molecule.

In another embodiment, an oligonucleotide of the invention is operably linked to a regulatory element (e.g., operably linked to a promoter in a vector construct). In some embodiments, the oligonucleotide is in the sense orientation. In other embodiments, the oligonucleotide is in the antisense orientation.

In a third aspect, the invention features a nucleic acid construct such as a vector (e.g., a plasmid, cosmid, viral particle or phage) that includes the sequence of a nucleic acid molecule or oligonucleotide described herein, operably linked to at least one regulatory element for expression or cloning, e.g., to a promoter. The vector may include additional elements, such as one or more of: an enhancer, a signal sequence, an origin of replication, one or more marker genes, and a transcription termination sequence.

In one embodiment, the vector is designed for expression of a Chinese hamster or CHO cell Ggta1 polypeptide described herein, in a host cell (e.g., a prokaryotic (e.g., *E. coli*) or eukaryotic cell (e.g., a mammalian cell such as a CHO cell)).

In one embodiment, the vector includes a DNA molecule of the invention cloned into the expression vector in an antisense orientation.

In one embodiment, the vector contains a nucleic acid molecule described herein, e.g., a Chinese hamster or CHO cell Ggta1 nucleic acid molecule described herein, configured to allow it to recombine into a specific site of a host cell's genome, e.g., configured to modify, disrupt or knock-out an endogenous Ggta1 gene in the host cell.

In a fourth aspect, the invention features isolated host cells transfected with a nucleic acid molecule, oligonucleotide, or nucleic acid construct described herein. The host cells may be prokaryotic (e.g., *E. coli*) or eukaryotic (e.g., plant cells, yeast cells or mammalian cells such as CHO cells). In one embodiment, the host cells are further genetically engineered to express a recombinant therapeutic glycoprotein.

In one embodiment, the host cells are CHO cells transfected with a nucleic acid molecule, oligonucleotide, or nucleic acid construct described herein (e.g., a vector that includes a Ggta1-a, Ggta1-b or Ggta1-c coding sequence described herein), wherein the CHO cells express increased levels of Ggta1 relative to the parent CHO cells. In such embodiments, the host cells may be capable of producing a glycoprotein (e.g., a recombinant therapeutic glycoprotein) with increased levels of terminal galactose-α1,3-galactose glycans compared to the parent cells. Methods of producing a glycoprotein (e.g., a recombinant therapeutic glycoprotein) having increased levels of terminal galactose-α1,3-galactose glycans by employing such host cells to produce the glycoprotein are also provided by the invention.

In another embodiment, the host cells are CHO cells transfected with a nucleic acid molecule, oligonucleotide, or nucleic acid construct described herein (e.g., transfected with a Ggta1-a, Ggta1-b or Ggta1-c dsRNA, siRNA, or knock-out vector), wherein the CHO cell has reduced expression of a Ggta1 described herein relative to an untransformed CHO cell, e.g., the host cells are Ggta1 knock-down or knock-out cells. In such embodiments, the host cells may be capable of producing a glycoprotein (e.g., a recombinant therapeutic glycoprotein) with lower levels of terminal galactose-α1,3-galactose glycans compared to the parent cells of the host cells. Methods of producing a glycoprotein (e.g., a recombinant therapeutic glycoprotein) having lower levels of terminal galactose-α1,3-galactose glycans by employing such host cells to produce the glycoprotein are also provided by the invention.

In a fifth aspect, the invention provides a process for modulating the glycan structure of a glycoprotein, e.g., a recombinant therapeutic glycoprotein, e.g., modulating the level of terminal galactose-α1,3-galactose glycans present in a recombinant therapeutic glycoprotein. The method includes culturing the host cells described herein (e.g., the Ggta1-transfected or Ggta1 knock-down or knock-out host cells) under conditions suitable for expression of the glycoprotein.

In a sixth aspect, the invention provides an isolated polypeptide that includes the amino acid sequence of a Ggta1 described herein, or an active fragment thereof. In one embodiment, the polypeptide includes an amino acid sequence encoded by any of the isolated nucleic acid sequences described herein.

In a specific embodiment, the polypeptide includes an amino acid sequence comprising the sequence of SEQ ID NO:2, SEQ ID NO:4 or SEQ ID NO:7.

In another embodiment, the polypeptide includes an amino acid sequence having at least about 90% sequence identity, e.g., at least about 91% sequence identity, e.g., at least about 92% sequence identity, e.g., at least about 93% sequence identity, e.g., at least about 94% sequence identity, e.g., at least about 95% sequence identity, e.g., at least about 96% sequence identity, e.g., at least about 97% sequence identity, e.g., at least about 98% sequence identity, e.g., at least about 99% sequence identity to the sequence of amino acid residues of SEQ ID NO:2, SEQ ID NO:4 or SEQ ID NO:7. The polypeptide may have one or more Ggta1 activity.

In another embodiment, the Ggta1 polypeptide, or fragment thereof, differs from the corresponding sequence of SEQ ID NO:2, SEQ ID NO:4 or SEQ ID NO:7. In one embodiment it differs by at least one but by less than 20, 15, 10 or 5 amino acid residues. In another it differs from the corresponding sequence in SEQ ID NO:2, SEQ ID NO:4 or SEQ ID NO:7 by at least one residue but less than 10% or 5% of the residues. In one embodiment, the differences include conservative substitutions. In another embodiment, the differences include non-conservative substitutions. The polypeptide may have one or more Ggta1 activity.

In one embodiment, a Ggta1 polypeptide described herein is linked to a heterologous amino acid sequence, e.g., the polypeptide is a Ggta1 fusion protein, e.g., an epitope-tagged Ggta1.

In a seventh aspect, the invention provides an antibody or antigen-binding fragment thereof, that specifically binds to a CHO cell or Chinese hamster Ggta1 polypeptide described herein. Optionally, the antibody is a monoclonal antibody, a functional antibody fragment (e.g., an Fab fragment) or a single chain antibody.

In one embodiment, the antibody or functional fragment thereof binds to a CHO cell or Chinese hamster Ggta1 with a greater binding affinity than to a naturally occurring Ggta1 from one or more of: mouse, rat, cow or dog. For example, the antibody or functional fragment thereof binds to a CHO cell or Chinese hamster Ggta1 with a 20%, 25%, 30%, 40%, 50%, 60% or greater affinity than to a naturally occurring Ggta1 from one or more of: mouse, rat, cow or dog. In one embodiment, the antibody or functional fragment thereof binds to a CHO cell or Chinese hamster Ggta1 described herein and does not bind to a naturally occurring Ggta1 from one or more of: mouse, rat, cow or dog. Binding affinity can be determined by a method known in the art, e.g., a radioimmune assay (RIA), ELISA, or binding in a column support format. Dissociation is performed by increasing denaturing conditions, or by competition with a related ligand. The dissociation constant, Kd, is determined by a Scatchard plot.

In an eighth aspect, the invention features methods to detect, and optionally quantify, Ggta1 expression and/or activity in CHO cells.

In one embodiment, the method include contacting a nucleic acid sample from a CHO cell population with a Chinese hamster or CHO cell Ggta1 oligonucleotide or isolated nucleic acid molecule described herein to obtain a value (e.g., a relative or absolute value) for the level of Ggta1 expression or activity in the CHO population. In one embodiment, the method includes employing a Ggta1 probe or primer or nucleic acid molecule described herein in an hybridization method (e.g., Southern or Northern blot), in-situ hybridization (e.g., fluorescence in situ hybridization or FISH), array hybridization, PCR (e.g., RT-PCR, qPCR) analysis, serial analysis of gene expression (SAGE), RNAase protection, branched DNA sandwich nucleic acid hybridization (e.g., Quantigene® system). In one embodiment, the CHO cells express a recombinant therapeutic glycoprotein. Such methods can be used, e.g., to screen CHO cell clones for differential expression of the Ggta1 gene.

In another embodiment, the method include contacting a protein sample from a CHO cell population with a Chinese hamster or CHO cell Ggta1 polypeptide or antibody described herein to obtain a value (e.g., a relative or absolute value) for the level of Ggta1 presence, expression or activity in the CHO population. In one embodiment, the method includes employing a Ggta1 antibody or fragment thereof described herein in an antibody-based detection method, e.g., enzyme linked immunosorbent assays (ELISAs), immunoprecipitations, immunofluorescence, enzyme immunoassay (EIA), radioimmunoassay (RIA), Western blot analysis, surface plasmon resonance (SPR). In one embodiment, the CHO cells express a recombinant therapeutic glycoprotein. Such methods can be used, e.g., to screen CHO cell clones for differential presence, expression or activity of Ggta1.

In one embodiment, the method includes performing a quantitative real time PCR reaction (qPCR) to assess Ggta1 expression in a CHO cell preparation. In one embodiment, the qPCR method employs a set of Ggta1 oligonucleotides described herein, e.g., employs a primer pair described herein (e.g., a primer pair described in Table 2 or Table 4).

In one embodiment, the value obtained for the level of Ggta1 expression or activity in the CHO population is compared to a reference value, e.g., a control value, a pre-determined value, or a value for Ggta1 expression or activity in a second CHO cell population. For example, the value obtained may be compared to a value obtained from CHO cells grown under different bioprocess conditions such as different media formulation and/or scale.

In a ninth aspect, the invention features a method of evaluating a sample derived from a CHO cell. The method includes providing a nucleic acid sample derived from a CHO cell, e.g., from a CHO cell that expresses a recombinant therapeutic glycoprotein, and determining a gene expression profile of the sample, wherein the profile includes a value representing the level of Ggta1 expression in the CHO cell, and a value representing the level of expression of another gene (e.g., another enzyme) in the CHO cell. The method may include contacting the sample with one or more Ggta1 nucleic acid molecules or probes or primer described herein. The method can further include comparing the value or profile (i.e., multiple values) to a reference value or reference profile. The gene expression profile of the sample can be obtained by any of the methods described herein (e.g., by providing a nucleic acid from the sample and contacting the nucleic acid to an array that includes a Ggta1 probe described herein). The method can be used to determine the level of Ggta1 expression or activity in a CHO cell, among the level of expression or activity of other genes.

In an tenth aspect, the invention features a two dimensional array having a plurality of addresses, each address of the plurality being positionally distinguishable from each other address of the plurality, and each address of the plurality having a unique capture probe, e.g., a nucleic acid or peptide sequence or antibody. At least one address of the plurality has a capture probe that recognizes a Ggta1 molecule described herein (e.g., a Ggta-1, Ggta1-b or Ggta1-c molecule described herein). In one embodiment, the capture probe is a nucleic acid, e.g., a probe complementary to a Ggta1 nucleic acid sequence. In another embodiment, the capture probe is a antibody, e.g., an antibody specific for a Ggta1 polypeptide described herein. Also featured is a method of analyzing a sample (e.g., a sample from a CHO cell) by contacting the sample to the aforementioned array and detecting binding of the sample to the array. Other features and advantages of the invention will be apparent from the following detailed description, and from the claims.

BRIEF DESCRIPTION OF THE FIGURES

FIGS. 2-1 and 2-2 are a multiple sequence alignment of Ggta1 from rat (NM_145674, with exon 5 and 6 deleted) (SEQ ID NO:58), mouse (NM_010283, full length) (SEQ ID NO:59), cow (NM_177511, full length) (SEQ ID NO:56), dog (XM_548478, full length) (SEQ ID NO:57), Chinese hamster ovary (consensus sequence) (SEQ ID NO:2), Chinese hamster spleen (consensus sequence)(SEQ ID NO:4), and CHO cell exons 8 and 9 at the amino acid level (SEQ ID NO:7). NCBI accession numbers are noted in parentheses.

FIGS. 3-1, 3-2, and 3-3 are the sequence of Ggta1-a cloned from Chinese hamster ovary-derived cDNA. The sequence is 1110 base pairs (SEQ ID NO:1) and translates to 370 amino acids (SEQ ID NO:2), a protein with a predicted molecular weight of 44,002 Daltons.

FIGS. 4-1, 4-2, and 4-3 are the sequence of Ggta1-b cloned from Chinese hamster derived-derived cDNA. The sequence is 1110 base pairs (SEQ ID NO:3) and translates to 370 amino acids (SEQ ID NO:4), a protein with a predicted molecular weight of 44,016 Daltons.

FIGS. 5-1, 5-2, 5-3, and 5-4 are the Ggta1 genomic sequence amplified from DHFR- CHO cell line. The sequence consists of exons 8 and 9 (UPPERCASE) with an intervening intron (in lowercase) (SEQ ID NO:5).

FIGS. 6-1and 6-2 are the translated amino acid sequence for CHO cell line Ggta1 exon 8 and 9. The sequence is 276 amino acids (SEQ ID NO:7), with a predicted molecular weight of 32,597 Daltons.

DETAILED DESCRIPTION

Figure 1:
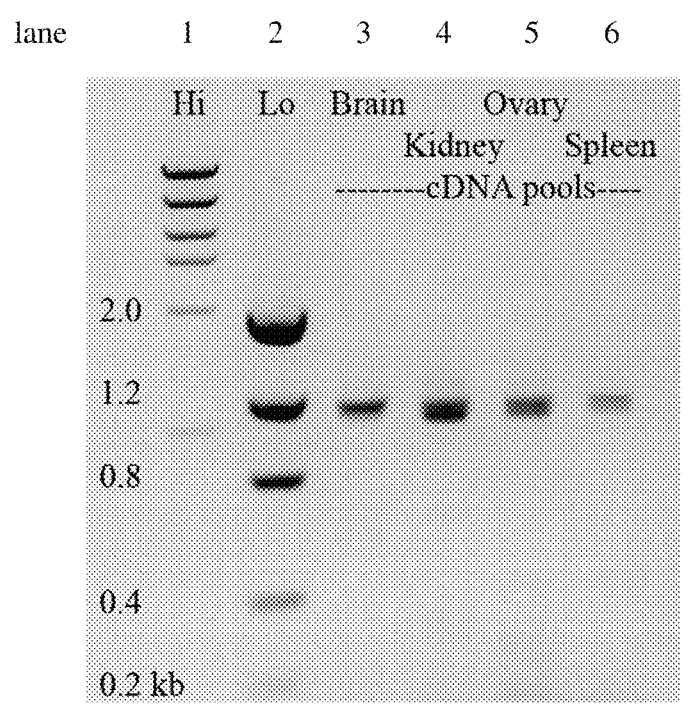
FIG. 1 is a photograph of an agarose gel electrophoretic separation of amplified Ggta1 PCR products from cDNA pools made from Chinese hamster brain (lane 3), kidney (lane 4), ovary (lane 5), and spleen (lane 6). Lanes 1 and 2 show size standards in kB. DNA is visualized by ethidium bromide staining.

The presence of terminal galactose-alpha-1-3-galactose residues (Gal-α-Gal) on recombinant glycoproteins in general represents an important posttranslational modification in large part due to the epitope's immunogenic potential and (consequently) regulatory importance in biologics development and manufacture. However, neither the expression of a Ggta1 gene or gene product, nor enzyme activity, has been reported to occur in any CHO cell line, historically the preferred mammalian expression platform for the commercial production of therapeutic biologics. In fact, the scientific literature suggests the opposite, namely that CHO cells are apparently incapable of producing N-glycans with terminal Gal-α-Gal structures due to either a lack of a functional copy of the Ggta1 gene in the Chinese Hamster genome or its expression at sufficient levels (Smith et al. (1990) *J Biol Chem* 265:6225-62343, 4); Takeuchi et al. (1989) *Proc Natl Acad Sci USA* 86:7819-7822).

The unexpected presence of terminal Gal-α-Gal residues in glycoproteins produced in CHO cells in particular is described in International Application Serial Number PCT/US2009/031678 (Publication Ref. WO 2010/085251), which is assigned to the assignee of the present application. The identification and cloning of 1,3 glycosyl transferase-1 (Ggta1) from Chinese hamster and from CHO cells, as described herein, provides a valuable tool to use in methods described herein to detect, measure and control Gal-α-Gal-containing glycans in a biological product.

Definitions

As used herein, the term "nucleic acid molecule" includes DNA molecules (e.g., a cDNA or genomic DNA), RNA molecules (e.g., an mRNA) and analogs of DNA or RNA. A DNA or RNA analog can be synthesized from nucleotide analogs. The nucleic acid molecule can be single-stranded or double-stranded.

The term "isolated nucleic acid molecule" or "purified nucleic acid molecule" includes nucleic acid molecules that are separated from other nucleic acid molecules present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and/or 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of 5' and/or 3' nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

As used herein, the term "hybridizes under high stringency" describes conditions for hybridization and washing in performing hybridization reactions. Such conditions can be found in Current Protocols in Molecular Biology, John Wiley & Sons, N.Y. (2007), Unit 6.3, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2× SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and 4) very high stringency hybridization conditions are 0.5M sodium phosphate, 7% SDS at 65° C., followed by one or more washes at 0.2×SSC, 1% SDS at 65° C.

As used herein, a "naturally-occurring" nucleic acid molecule refers to an RNA or DNA molecule having a nucleotide sequence that occurs in nature. For example a naturally occurring nucleic acid molecule can encode a natural protein expressed by a wild type cell.

As used herein, the terms "gene" and "recombinant gene" refer to nucleic acid molecules which include at least an open reading frame encoding a Ggta1 protein. The gene can optionally further include non-coding sequences, e.g., regulatory sequences and introns.

An "isolated" or "purified" polypeptide or protein is substantially free of cellular material or other contaminating proteins from the cell or tissue source from which the protein is derived, or substantially free from chemical precursors or other chemicals when chemically synthesized. "Substantially free" means that a preparation of Ggta1 protein is at least 50% Ggta1 protein by weight. In a preferred embodiment, the preparation of Ggta1 protein has less than about 30%, 20%, 10% and more preferably 5% (by dry weight), of non-Ggta1 protein (also referred to herein as a "contaminating protein"), or of chemical precursors or non-Ggta1 chemicals. When the Ggta1 protein or biologically active portion thereof is recombinantly produced, it is also preferably substantially free of culture medium, i.e., culture medium represents less than about 20%, more preferably less than about 10%, and most preferably less than about 5% of the volume of the protein preparation.

A "Ggta1 polypeptide", as that term is used herein, refers to a polypeptide that (1) shows an overall sequence identity to one or more of SEQ ID NO:2, 4, or 7 of at least about 90%; (2) includes at least one characteristic sequence element found in SEQ ID NO:2, 4, or 7; and/or (3) shares at least one biological activity found in a polypeptide of SEQ ID NO:2, 4, or 7. In some embodiments, a Ggta1 polypeptide shows an overall sequence identity to one or more of SEQ ID NO:2, 4, or 7 of at least about 90%, at least about 91%, at least about 92%, at least about 93%, at least about 94%, at least about 95%, at least about 96%, at least about 97%, at least about 98%, at least about 99% or more. In some embodiments, a Ggta1 polypeptide includes at least one sequence element characteristic sequence element found in SEQ ID NO:2, 4, or 7 and also shows an overall sequence identity to SEQ ID NO:2, 4, or 7 that is at least about at least about 90%, at least about 91%, at least about 92%, at least about 93%, at least about 94%, at least about 95%, at least about 96%, at least about 97%, at least about 98%, at least about 99% or more. In some embodiments, a Ggta1 polypeptide has a length that is at least about at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or more of the length of SEQ ID NO:2, 4, or 7. In some embodiments, a Ggta1 polypeptide is a fragment of SEQ ID NO:2, 4, or 7. In some embodiments, a Ggta1 polypeptide shows at least about 90%, at least about 91%, at least about 92%, at least about 93%, at least about 94%, at least about 95%, at least about 96%, at least about 97%, at least about 98%, at least about 99% or more identity to a fragment of SEQ ID NO:2, 4, or 7; in some such embodiments, the fragment is at least about 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 150, 200, 250, 300, 350, or more amino acids long.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a Ggta1 protein is preferably replaced with another amino acid residue from the same side chain family. Alternatively, in another embodiment, mutations can be introduced randomly along all or part of a Ggta1 coding sequence, such as by saturation mutagenesis, and the resultant mutants can be screened for Ggta1 activity to identify mutants that retain activity. Following mutagenesis, the encoded protein can be expressed recombinantly and the activity of the protein can be determined.

"Percent (%) sequence identity" with respect to the sequences identified herein is defined as the percentage of amino acid residues or nucleotides in a candidate sequence that are identical with the amino acid residues or nucleotides in the reference sequence, after aligning the sequences and introducing gaps, if necessary, to achieve the maximum percent sequence identity. (E.g., gaps can be introduced in one or both of a first and a second amino acid or nucleic acid sequence for optimal alignment and non-homologous sequences can be disregarded for comparison purposes). Alignment for purposes of determining percent sequence identity can be achieved in various ways that are within the skill in the art, for instance, using publicly available computer software such as BLAST, ALIGN or Megalign (DNASTAR) software. Those skilled in the art can determine appropriate parameters for measuring alignment, including any algorithms needed to achieve maximal alignment over the full length of the sequences being compared. In one embodiment, the length of a reference sequence aligned for comparison purposes is at least 30%, e.g., at least 40%, e.g., at least 50%, 60%, 70%, 80%, 90%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

A "characteristic sequence element", as that term is used herein, refers to a set of amino acids whose identity and relative positions with respect to one another confer onto a particular polypeptide one or more activities or features of interest. In some embodiments, a characteristic sequence element is one that is unique to the particular polypeptide in that it is not found in known polypeptides that lack the activity or feature. In some embodiments, a characteristic sequence element comprises at least 5, 6, 7, 8, 9, 10, 11, 12, 13, 14, 15, 16, 17, 18, 19, 20, 21, 22, 23, 24, 25, 26, 27, 28, 29, 30 or more amino acids. In some embodiments, some or all amino acids that participate in a characteristic sequence element are contiguous to one another; in some embodiments, certain residues within a characteristic sequence element may be separated from one or more other residues in linear order. In some embodiments, a characteristic sequence element comprises residues that are located near one another in three-dimensional space when a polypeptide chain is folded.

A "preparation of cells", as used herein, refers to an in vitro preparation of cells. In the case of cells from multicellular organisms (e.g., plants and animals), a purified preparation of cells is a subset of cells obtained from the organism, not the entire intact organism. In the case of unicellular microorganisms (e.g., cultured cells and microbial cells), it consists of a preparation of at least 10% and more preferably 50% of the subject cells.

Various aspects of the invention are described in further detail below.

Ggta1 Nucleic Acid Molecules

In one aspect, the invention provides isolated or purified Ggta1 nucleic acid molecules as described herein. A provided nucleic acid molecule may encode Ggta1 polypeptide described herein, e.g., a full-length Ggta1 protein or an active fragment thereof (e.g., a catalytically active fragment thereof). Also included are Ggta1 nucleic acid molecules or fragments thereof that may not encode a functional protein but can be used, e.g., to construct a vector to target an endogenous Chinese hamster or CHO cell Ggta1 gene, e.g., to knock out or modify the sequence of an endogenous Ggta1 gene.

In some embodiments, provided Ggta1 nucleic acid molecules are derived from Chinese hamster or from CHO cells. In some embodiments, provided Ggta1 nucleic acid molecules have a nucleotide sequence that is identical to that of a Ggta1 nucleic acid molecule derived from Chinese hamster or from CHO cells. In some embodiments, provided Ggta1 nucleic acid molecules encode a Ggta1 polypeptide that is derived from Chinese hamster or CHO cells.

In one embodiment, an isolated nucleic acid molecule of the invention has a nucleotide sequence of SEQ ID NO:1, 3, 5 or 6, or a portion of any of these nucleotide sequences. In some embodiments, the nucleic acid molecule includes coding sequence only. In other embodiments, the nucleic acid molecule includes non-coding sequence, such as 5' untranslated sequences or intron sequence. Both sense and antisense sequences are included.

Also included are oligonucleotides or fragments of the nucleic acid molecules that are suitable for use as probes, tags, or primers, e.g., to detect and/or quantify Ggta1 expression. Such oligonucleotides or fragments may be at least about 10, 12 or 15, about 20 or 25, or about 30, 35, 40, 45, 50, 55, 60, 65, or 75 consecutive nucleotides of SEQ ID NO:1, 3, 5 or 6. In certain embodiments, oligonucleotides are less than about 500, 400, 300, 200, 150, 120, or 100 nucleotides in length. In one embodiment, a probe or primer is attached to a solid support, e.g., a solid support described herein. In another embodiment a set of primers is provided, e.g., primers suitable for use in a PCR reaction, which can be used to amplify a selected region of a Ggta1 sequence, e.g., a domain, region, site or other sequence described herein. The primers may be at least 5, 10, or 50 base pairs in length and less than 100, or less than 200, base pairs in length. The primers should be identical, or differ by one base from a sequence disclosed herein or from a naturally occurring variant. For example, primers suitable for amplifying all or a portion of a Ggta1 sequence described herein are disclosed in Table 2 and Table 4. In one embodiment, a kit of primers includes a forward primer that anneals to a coding strand and a reverse primer that anneals to the non-coding strand of SEQ ID NO:1, 3, 5 or 6.

Nucleic acid oligonucleotides, e.g., probes, tags or primers described herein can be labeled. Typically, such labels are chemiluminescent, fluorescent, radioactive, or colorimetric.

A nucleic acid of the invention may be recombinantly produced, or synthetically produced.

Ggta1 Nucleic Acid Variants:

The invention encompasses nucleic acid molecules that differ from the nucleotide sequences disclosed herein as SEQ ID NO:1, 3, 5 or 6. For example, an isolated nucleic acid molecule of the invention can have a sequence related to SEQ ID NO:1, 3, 5 or 6, or to a portion of any of these nucleotide sequences, e.g., related by a specified level of sequence identity or ability to hybridize under high stringency conditions. A nucleic acid of the invention may have a naturally occurring sequence (e.g., the sequence of a naturally occurring allelic variant or mutant) or it may have a non-naturally occurring sequence. In one embodiment, differences can be due, e.g., to degeneracy of the genetic code (and result in a nucleic acid which encodes the same Ggta1 proteins as those encoded by the nucleotide sequence disclosed herein). Nucleic acids of the inventor can be chosen for having codons which are preferred, or non-preferred, for a particular expression system. E.g., the nucleic acid can be one in which at least one codon, e.g., at least 10%, or 20% of the codons, has been altered such that the sequence is optimized for expression in a particular system, e.g., E. coli, yeast, human, insect, or CHO cells.

Nucleic acid variants can be naturally occurring, such as allelic variants (same locus), homologs (different locus), or can be non-naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product). Nucleic acid modification and mutagenesis techniques are known in the art.

Allelic variants of Ggta1, e.g., CHO Ggta1, include both functional and non-functional proteins. Functional allelic variants are naturally occurring nucleotide sequences that encode variants of the Ggta1 protein that maintain the ability to provide the enzymatic function. Functional allelic variants will typically contain conservative substitution of one or more amino acids of SEQ ID NO:2, 4 or 7, or substitution, deletion or insertion of non-critical residues in non-critical regions of the protein. Non-functional allelic variants are naturally-occurring nucleotide sequence variants that encode a Ggta1 polypeptide that does not preserve the enzymatic function. Non-functional allelic variants will typically contain a non-conservative substitution, a deletion, or insertion, or premature truncation of the amino acid sequence of SEQ ID NO:2, 4 or 7, or a substitution, insertion, or deletion in critical residues or critical regions of the protein.

Ggta1 Antisense Molecules:

Also included in the invention are isolated nucleic acid molecules that are antisense to a Chinese hamster or CHO cell Ggta1 described herein. The major classes of antisense agents are antisense oligonucleotides (ODNs), ribozymes, DNAzymes and RNA interference (RNAi). Such molecules can be used in methods to inhibit Ggta1 activity, e.g., in CHO cells. An "antisense" nucleic acid has a nucleotide sequence that is complementary to a target nucleic acid. An antisense nucleic acid can be designed such that it is complementary to the entire coding region of a Ggta1 mRNA, but more preferably is an oligonucleotide which is antisense to only a portion of the coding or noncoding region of a Ggta1 mRNA. For example, the antisense oligonucleotide can be complementary to the region surrounding the translation start site of Ggta1 mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length. An antisense molecule will inhibit the production of Ggta1 described herein An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation. The antisense nucleic acid molecules can be delivered to cells using vectors described herein. To achieve sufficient intracellular concentrations of the antisense molecules, vector constructs in which the antisense nucleic acid molecule is placed can be under the control of a strong pol II or pol III promoter.

Methods of making and using antisense molecules to modulate biological activities are known in the art, see for example: Pan and Clawson, *Antisense applications for biological control* (2006) J. Cell Biochem. 98(1):14-35; Sioud and Iversen, *Ribozymes, DNAzymes and small interfering RNAs as therapeutics* (2005) Curr Drug Targets 6(6):647-53; Bhindi et al., *Brothers in arms: DNA enzymes, short interfering RNA, and the emerging wave of small-molecule nucleic acid-based gene-silencing strategies* (2007) Am J. Pathol. 171(4):1079-88.

Ggta1 Polypeptides

In another aspect, the invention features an isolated Ggta1 polypeptides or proteins (or biologically active fragments thereof) as described herein. Typically, a biologically active fragment of a Ggta1 protein has one or more of the following characteristics: it has the ability to catalyze the synthesis of an Gal-α1,3-Gal glycan; it utilizes UDP-Gal to transfer a galactose moiety onto an existing N-linked glycan that contains Gal so as to generate a Gal-α-Gal structure and UDP; it utilizes UDP-Gal to transfer a galactose moiety onto an existing O-linked glycan that contains Gal so as to generate a Gal-α-Gal structure and UDP; it utilizes UDP-Gal to transfer a galactose moiety onto an existing glycolipid that contains Gal so as to generate a Gal-α-Gal structure and UDP; binds to UDP-Gal and a glycan terminating in galactose; binds to Gal-α-Gal containing structures; hydrolyzes UDP-Gal to Gal; localizes to the Golgi compartment if transfected and expressed in a eukaryotic cell; binds to a Chinese hamster- or CHO cell-specific anti-Ggta1 antibody; can utilize chemically modified UDP-Gal analogs (e.g., thiosugar, trinitrophenyl, 2 deoxy, 2 azido, radiochemically labeled such as 3H, Cl4,33P, 32P) to transfer a galactose moiety onto an existing N- or O-linked glycan.

Ggta1 polypeptides or proteins (or fragments thereof) can be isolated from cells or tissue sources using standard protein purification techniques. In some embodiments, Ggta1 polypeptides or proteins are isolated from Chinese hamster or from CHO cells. Ggta1 polypeptides or proteins (or fragments thereof) can be produced by recombinant DNA techniques or synthesized chemically.

Polypeptides of the invention include those which arise as a result of the existence of multiple genes, alternative transcription events, alternative RNA splicing events, and alternative translational and post-translational events. The polypeptide can be expressed in systems, e.g., cultured cells, which result in substantially the same post-translational modifications present when expressed the polypeptide is expressed in a native cell, or in systems which result in the alteration or omission of post-translational modifications, e.g., glycosylation or cleavage, present when expressed in a native cell.

In some embodiments, a Ggta1 polypeptide of the invention has the sequence of SEQ ID NO:2, 4 or 7 or a functional fragment thereof. Other embodiments include a protein that contains at least one different amino acid residue from SEQ ID NO:2, 4 or 7, but no more than 10%. The differences may be in amino acid residues that are not essential for activity. In some embodiments, the differences are conservative substitutions or differences or changes at a non essential residue. Also included are polypeptide sequences that are highly related to SEQ ID NO:2, 4 or 7 by a specified percent of sequence identity.

The invention includes Ggta1 chimeric or fusion proteins. As used herein, a Ggta1 "chimeric protein" or "fusion protein" includes a Ggta1 polypeptide linked to a non-Ggta1 polypeptide. The non-Ggta1 polypeptide can be fused to the N-terminus or C-terminus of the Ggta1 polypeptide, or can be fused internally. In one example, the fusion protein can include a moiety which has a high affinity for a ligand. For example, the fusion protein can be a GST-Ggta1 fusion protein in which the Ggta1 sequences are fused to the C-terminus of the GST sequences. Such fusion proteins can facilitate the purification of recombinant Ggta1. Expression vectors are commercially available that encode a fusion moiety (e.g., a GST polypeptide). A Ggta1-encoding nucleic acid can be cloned into such an expression vector such that the fusion moiety is linked in-frame to the Ggta1 protein.

Alternatively, the fusion protein can be a Ggta1 protein containing a heterologous signal sequence at its N-terminus. In certain host cells (e.g., mammalian host cells), expression and/or secretion of Ggta1 can be increased through use of a heterologous signal sequence.

Fusion proteins can include all or a part of a serum protein, e.g., an IgG constant region, or human serum albumin.

Variants of Ggta1 Polypeptides:

In another aspect, the invention also features a variant of a Ggta1 polypeptide, e.g., which functions as an agonist (mimetic) or as an antagonist. Variants of the Ggta1 proteins can be generated by mutagenesis, e.g., discrete point mutation, the insertion or deletion of sequences or the truncation of a Ggta1 protein. An agonist of the Ggta1 proteins can retain substantially the same, or a subset, of the biological activities of the naturally occurring form of a Ggta1 protein. An antagonist of a Ggta1 protein can inhibit one or more of the activities of the naturally occurring form of the Ggta1 protein by, for example, competitively modulating a Ggta1-mediated activity of a Ggta1 protein.

In some embodiments, a variant of a Ggta1 polypeptide shares the amino acid sequence of a "parent" Ggta1 polypeptide (or variant Ggta1 polypeptide) but includes one or more covalent modifications as compared to the parent polypeptide. For example, in some embodiments, variants are PEGylated, glycosylated, phosphorylated, etc.

Variants of a Ggta1 protein can be identified by screening combinatorial libraries of mutants, e.g., truncation mutants, of a Ggta1 protein for agonist or antagonist activity.

Variants of Ggta1 polypeptides, like Ggta1 polypeptides, may be produced as fusion proteins.

Ggta1 Antibodies and Antibody Production

In another aspect, the present invention provides an antibody that binds specifically to a Ggta1 polypeptide (and/or to a Ggta1 polypeptide variant) as described herein; the present invention also provides methods for producing such antibody. The term "antibody" refers to a protein that includes at least one immunoglobulin variable domain or immunoglobulin variable domain sequence capable of binding a Chinese hamster or CHO Ggta1 antigen. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. As such, the term "antibody" encompasses polyclonal, monospecific, monoclonal, monovalent, chimeric, humanized, human, bispecific, and heteroconjugate antibodies as well as antigen-binding fragments of these.

The term "antigen-binding fragment" of a full length antibody, as used herein, refers to one or more fragments of a full-length antibody that retain the ability to specifically bind to a target of interest. Examples of such fragments include (i) a Fab fragment, a monovalent fragment consisting of the VL, VH, CL and CH1 domains; (ii) a F(ab')2 fragment, a bivalent fragment including two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment, which consists of a VH domain; and (vi) an isolated complementarity determining region (CDR) that retains functionality.

Isolated Ggta1 proteins (including variants) or antigenic fragments thereof can be used as an antigens for producing, screening or selecting such antibodies. Antibodies and antigen-binding fragments thereof can be obtained using any appropriate technique including conventional hybridoma techniques, recombinant techniques, combinatorial methods, phage display techniques, and others known to those with skill in the art. For example, see *Antibody Engineering Methods and Protocols*, Benny K. C. Lo, Ed. (Humana Press, 2003); *Making and Using Antibodies: A Practical Handbook*, Gary Howard and Matthew Kaser, Eds. (CRC, 2006); *Antibody Phage Display: Methods and Protocols*, Philippa Obrien and Robert Aitken, Eds. (Humana Press, 2001); *Monoclonal Antibodies: Methods and Protocols*, Maher Albitar, Ed. (Humana Press, 2007).

An antibody of the invention can be coupled to a second functional moiety, e.g., the antibody can be coupled to a label, e.g., a fluorescent label, radioactive label, imaging agent.

In some embodiments, an anti-Ggta1 antibody can be used to detect a Ggta1 polypeptide (e.g., in a cellular lysate or cell supernatant) in order to detect and optionally measure the presence, level, abundance or pattern of expression of the protein. Detection can be facilitated by coupling (i.e., physically linking) the antibody to a detectable substance (i.e., antibody labelling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, .beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin.

Recombinant Expression Vectors

In another aspect, the invention includes vectors (e.g., expression vectors, knock-out vectors, or vectors driving antisense sequences) containing a nucleic acid described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA.

A vector can include a Chinese hamster or CHO cell Ggta1 nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., Ggta1 proteins, mutant forms of Ggta1 proteins, fusion proteins, and the like).

The recombinant expression vectors of the invention can be designed for expression of Ggta1 polypeptides in prokaryotic or eukaryotic cells. For example, polypeptides of the invention can be expressed in *E. coli*, insect cells (e.g., using baculovirus expression vectors), yeast cells or mammalian cells, preferably CHO cells. When used in mammalian cells, the expression vector's control functions can be provided by viral regulatory elements. For example, commonly used promoters are derived from polyoma, Adenovirus 2, cytomegalovirus and Simian Virus 40.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Purified fusion proteins can be used in Ggta1 activity assays, (e.g., direct assays or competitive assays), or to generate antibodies specific for Ggta1 proteins.

In another embodiment, the promoter is an inducible promoter, e.g., a promoter regulated by a steroid hormone, by a polypeptide hormone (e.g., by means of a signal transduction pathway), or by a heterologous polypeptide (e.g., the tetracycline-inducible systems, "Tet-On" and "Tet-Off" from Clontech Inc., CA.

The invention further provides a recombinant expression vector comprising a DNA molecule of the invention cloned into the expression vector in an antisense orientation. Regulatory sequences (e.g., viral promoters and/or enhancers)

operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus.

Another aspect of the invention provides a vector containing a nucleic acid molecule described herein, e.g., a Chinese hamster or CHO cell Ggta1 nucleic acid molecule described herein, configured to allow it to homologously recombine into a specific site of a host cell's genome, e.g., configured to modify, disrupt or knock-out an endogenous Ggta1 gene in the host cell.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation DEAE-dextran-mediated transfection, lipofection, or electroporation.

Alternatively, a recombinant expression vector can be transcribed and translated in vitro, for example using T7 promoter regulatory sequences and T7 polymerase.

Methods to make and use vectors including the nucleic acids described herein are known in the art. For example, methods are provided in *Current Protocols in Molecular Biology* (2007, John Wiley and Sons, Inc., Print ISSN: 1934-3639).

Host Cells/Genetically Engineered Cells

A host cell (e.g., a host cell containing any vector described herein) can be any prokaryotic or eukaryotic cell. For example, a Ggta1 protein can be expressed in bacterial cells (such as *E. coli*), plant cells, insect cells, yeast or mammalian cells (such as CHO cells). Other suitable host cells are known to those skilled in the art.

An isolated cell of the invention can be a cell genetically engineered to express increased levels of Chinese hamster or CHO cell Ggta1 relative to the parent cell. Accordingly, the invention also provides methods for producing a Ggta1 protein using the host cells of the invention. In one embodiment, the method includes culturing the host cell of the invention (into which a recombinant expression vector encoding a Ggta1 protein has been introduced) in a suitable medium such that a Ggta1 protein is produced. In another embodiment, the method further includes isolating a Ggta1 protein from the medium or the host cell.

In another aspect, the invention features, a cell or purified preparation of cells which include a Chinese hamster or CHO cell Ggta1 transgene, or which otherwise misexpress Ggta1. For example, an isolated cell of the invention is a cell (e.g., a CHO cell) genetically engineered to express lower levels of Ggta1 than the parent cell, e.g., the cell is a Ggta1 knock-out or knock-down CHO cell. The generation of knock-out or knock-down cells for reducing or inhibiting expression of endogenous proteins is a known technique. For example, a CHO knock-out cell was recently described in Yamane-Ohnuki et al. (2004) *Biotechnol. Bioeng* 87:614-622.

A cell preparation can consist of isolated human or non-human cells, e.g., rodent cells, e.g., hamster-derived, mouse or rat cells, rabbit cells, or pig cells or cell lines, e.g., a CHO cell line. CHO cells useful as host cells of the invention include cells of any strain of CHO, including CHO K1 (ATCC CCL-61), CHO pro3-, CHO DG44, CHO-S, CHO P12 or the dhfr-CHO cell line DUK-BII (Chassin et al., PNAS 77, 1980, 4216-4220).

Methods to make and use host cells of the invention, and to make therapeutic glycoproteins in such host cells are known in the art. For example, methods are provided in *Current Protocols in Cell Biology* (2007, John Wiley and Sons, Inc., Print ISSN: 1934-2500); *Current Protocols in Protein Science* (2007, John Wiley and Sons, Inc., Print ISSN: 1934-3655); Wurm, *Production of recombinant protein therapeutics in cultivated mammalian cells* (2004) *Nature Biotech.* 22:1393-1398; *Therapeutic Proteins: Methods and Protocols*, Smales and James, eds. (2005, Humana Press, ISBN-10: 1588293904).

Methods to Detect Ggta1 Expression or Activity

The ability to monitor the expression and/or activity of $\alpha$-1,3 glycosyl transferase-1 (Ggta1) responsible for the enzymatic addition of the Gal-alpha-Gal epitope on N-glycans is a valuable tool to predict the potential for the epitope's existence in a particular cell line or clonal population. Accordingly, the invention also features methods of evaluating Ggta1 expression in CHO cells. The method includes providing a sample from a population of CHO cells, and contacting the sample with a Ggta1 nucleic acid or antibody described herein.

These methods can be used to profile relative Ggta1 expression in cells of potentially differing background or clonal phenotype. It can likewise be used to assess changes in gene expression when such cells are grown under different bioprocess conditions such as media formulation and/or scale. For example, such methods can be used to evaluate Ggta1 activity or Gal-alpha-Gal presence or level in a CHO cell population that expresses or produces a therapeutic glycoprotein. In some embodiments, the CHO cell population is a population in a bioreactor, e.g., a commercial bioreactor. Such methods can be used, e.g., to monitor Ggta1 expression during a manufacturing process. In other embodiments, the CHO cell population is one of a plurality of CHO cell populations that are screened for Ggta1 activity. The plurality of CHO cells being screened may differ in any number of ways, e.g., they may differ in genetic background, growth conditions, etc. In such screening methods, CHO cells can be selected based on the level of Ggta1 activity, e.g., selected as suitable hosts for producing a particular therapeutic glycoprotein. Ggta1 activity in the CHO cells being evaluated can be compared to a reference level of Ggta1 activity, e.g., a control level, a pre-specified level, or a level corresponding to the level in a second CHO cell population.

Nucleic acid based-detection methods encompass hybridization or amplification assays that include, but are not limited to, Southern or Northern analyses, polymerase chain reaction analyses (e.g., quantitative PCR), SAGE analyses, probe arrays or oligonucleotide arrays.

One method for the detection of Ggta1 expression involves contacting a sample of isolated mRNA from a CHO cell population with a nucleic acid molecule (e.g., probe) described herein that can hybridize to the mRNA encoded by the Ggta1 gene. Another method for the detection of Ggta1 expression involves contacting a sample of mRNA or cDNA from a CHO cell population with a primer pair described herein to amplify a Ggta1 sequence. The level of Ggta1 mRNA in a sample can be evaluated, e.g., by rtPCR, qPCR, ligase chain reaction, self sustained sequence replication, rolling circle replication, or any other nucleic acid amplification method, followed by the detection of the amplified molecules using techniques known in the art. Real-time, quantitative PCR (or qPCR) represents one example of a specific and highly sensitive molecular profiling method to quantify the gene expression levels of Ggta1 in a limited number of cells.

As used herein, an appropriate primer pair is defined as a pair of oligonucleotides that can anneal to 5' and 3' regions of a gene (plus and minus strands, respectively, or vice-versa) defining a region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

The level of Ggta1 gene expression in a cell (e.g., a CHO cell) can be determined both by in situ or by in vitro formats. In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array described below. A skilled artisan can adapt known mRNA detection methods for use in detecting the level of mRNA encoded by a Ggta1 gene. For in situ methods, a cell or tissue sample can be prepared/processed and immobilized on a support, typically a glass slide, and then contacted with a probe that can hybridize to a Ggta1 gene being analyzed.

In another embodiment, the methods further include contacting a control sample with a compound or agent capable of detecting Ggta1 mRNA, or genomic DNA, and comparing the presence of Ggta1 mRNA or genomic DNA in the control sample with the presence of Ggta1 mRNA or genomic DNA in the test sample. In still another embodiment, serial analysis of gene expression, e.g., as described in U.S. Pat. No. 5,695,937, is used to detect Ggta1 transcript levels.

Antibody-based techniques for detection of Ggta1 protein include enzyme linked immunosorbent assays (ELISAs), immunoprecipitations, immunofluorescence, enzyme immunoassay (EIA), radioimmunoassay (RIA), Western blot analysis, surface plasmon resonance. Other methods may include the detection of Ggta1 peptides or fragments thereof using mass spectrometric-based methods, including, but not limited to LC-MS, MS/MS, MS/MS/MS, MALDI-MS, multiple reaction monitoring (MRM).

In one embodiment, detection methods described herein are part of determining a gene expression profile of the sample, wherein the profile includes a value representing the level of Ggta1 expression, among at least one other value for expression of at least one other gene. The method can further include comparing the value or the profile (i.e., multiple values) to a reference value or reference profile. The gene expression profile of the sample can be obtained by any of the methods described herein (e.g., by providing a nucleic acid from the sample and contacting the nucleic acid to an array). The method can be used to evaluate or screen CHO cells.

In another aspect, the invention features a computer medium having a plurality of digitally encoded data records. Each data record includes a value representing the level of expression of Chinese hamster or Ggta1 in a sample, and a descriptor of the sample. The descriptor of the sample can be an identifier of the sample, e.g., the cell type from which the sample was derived (e.g., a CHO cell strain), or a cell culture condition under which the cell that is the source of the sample was cultured. In one embodiment, the data record further includes values representing the level of expression of genes other than Ggta1 (e.g., other genes associated with glycan synthesis, or other genes on an array). The data record can be structured as a table, e.g., a table that is part of a database such as a relational database (e.g., a SQL database of the Oracle or Sybase database environments).

Arrays and Uses Thereof

The invention also features a two dimensional array having a plurality of addresses, each address of the plurality being positionally distinguishable from each other address of the plurality. Each address of the plurality has a unique capture probe, e.g., a nucleic acid or polypeptide sequence or antibody described herein. At least one address of the plurality has a capture probe that recognizes a Chinese hamster or CHO cell Ggta1 molecule described herein (e.g., a Ggta-1, Ggta1-b or Ggta1-c molecule described herein). In one embodiment, the capture probe is a nucleic acid, e.g., a probe complementary to a Ggta1 nucleic acid sequence. In another embodiment, the capture probe is an antibody, e.g., an antibody specific for a Ggta1 polypeptide described herein. Also featured is a method of analyzing a sample (e.g., a sample from a CHO cell) by contacting the sample to the aforementioned array and detecting binding of the sample to the array.

The array can have a density of at least than 10, 50, 100, 200, 500, 1,000, 2,000, or 10,000 or more addresses/cm$^2$, and ranges between. In a preferred embodiment, the plurality of addresses includes at least 10, 100, 500, 1,000, 5,000, 10,000, 50,000 addresses. In a preferred embodiment, the plurality of addresses includes equal to or less than 10, 100, 500, 1,000, 5,000, 10,000, or 50,000 addresses. The substrate can be a two-dimensional substrate such as a glass slide, a wafer (e.g., silica or plastic), a mass spectroscopy plate, or a three-dimensional substrate such as a gel pad. Addresses in addition to address of the plurality can be disposed on the array.

An array can be generated by various methods, e.g., by photolithographic methods (see, e.g., U.S. Pat. Nos. 5,143,854; 5,510,270; and 5,527,681), mechanical methods (e.g., directed-flow methods as described in U.S. Pat. No. 5,384,261), pin-based methods (e.g., as described in U.S. Pat. No. 5,288,514), and bead-based techniques (e.g., as described in PCT US/93/04145).

In another aspect, the invention features a method of analyzing the expression of Ggta1. The method includes providing an array as described above; contacting the array with a sample and detecting binding of a Ggta1-molecule (e.g., nucleic acid or polypeptide) to the array. In a preferred embodiment, the array is a nucleic acid array. Optionally the method further includes amplifying nucleic acid from the sample prior to or during contact with the array.

In another embodiment, the array can be used to assay gene expression in a cell population (e.g., a CHO cell population), particularly the expression of Ggta1. If a sufficient number of diverse samples is analyzed, clustering (e.g., hierarchical clustering, k-means clustering, Bayesian clustering and the like) can be used to identify other genes which are co-regulated with Ggta1. For example, the array can be used for the quantitation of the expression of multiple genes. Thus, not only cell-type specificity, but also the level of expression of a battery of genes in the tissue may be ascertained. Quantitative data can be used to group (e.g., cluster) genes on the basis of their tissue expression per se and level of expression in that tissue.

In one example, array analysis of gene expression can be used to assess the effect of differing cell culture conditions on Ggta1 expression. A first cell population can be cultured under a first set of conditions, and a second cell population can be cultured under a second set of conditions and nucleic acid from the plurality of populations can be analyzed on such an array. In this context, the effect of culture conditions on biological response can be determined. Similarly, CHO cells having different genetic backgrounds can be compared.

Methods of Modulating Glycoprotein Glycan Structure

The invention features methods of producing a glycoprotein in CHO cells, where the glycoprotein has altered levels of Gal-alpha-Gal glycan structures, e.g., relative to a glycoprotein in the prior art, e.g., relative to a glycoprotein marketed as a therapeutic glycoprotein. The method includes culturing host cells described herein (e.g., the Ggta1-transfected or Ggta1 knock-down or knock-out host cells) under conditions suitable for expression of the glycoprotein. The glycoprotein can be selected from those described in Table 5.

In one embodiment, a glycoprotein is produced having increased levels of Gal-alpha-Gal glycan structures relative to a glycoprotein in the prior art having the same or highly similar polypeptide sequence (e.g., at least 90%, 91%, 92%, 93%, 94%, 95%, 96%, 97%, 98%, 99% identical polypeptide sequence). The method includes culturing a CHO host cell described herein that has been genetically engineered to produce increased levels of Chinese hamster or CHO cell Ggta1 relative to the parent cell (e.g., a Ggta1 overexpressing CHO cell), where the host cell also contains a transgene encoding a therapeutic glycoprotein, and purifying the therapeutic glycoprotein from the resulting cultured cells.

In another embodiment, a glycoprotein is produced having reduced levels of Gal-alpha-Gal glycan structures relative to a glycoprotein in the prior art having the same or highly similar polypeptide sequence (e.g., at least 90%, 91%, 92%, 93%, 94%, 95%, 96%, 97%, 98%, 99% identical polypeptide sequence). The method includes culturing a CHO host cell described herein that has been genetically engineered to produce reduced levels of Chinese hamster or CHO cell Ggta1 relative to the parent cell (e.g., a Ggta1 knock-out or knock-down CHO cell described herein), where the host cell contains a transgene encoding a therapeutic glycoprotein, and purifying the therapeutic glycoprotein from the resulting cultured cells. Such glycoproteins thus produced can provide improved versions of marketed therapeutic glycoproteins.

TABLE 5

| Protein Product | Reference Drug |
| --- | --- |
| interferon gamma-1b | Actimmune ® |
| alteplase; tissue plasminogen activator | Activase ®/ Cathflo ® |
| Recombinant antihemophilic factor | Advate |
| human albumin | Albutein ® |
| laronidase | Aldurazyme ® |
| interferon alfa-N3, human leukocyte derived | Alferon N ® |
| human antihemophilic factor | Alphanate ® |
| virus-filtered human coagulation factor IX | AlphaNine ® SD |
| Alefacept; recombinant, dimeric fusion protein LFA3-Ig | Amevive ® |
| bivalirudin | Angiomax ® |
| darbepoetin alfa | Aranesp ™ |
| bevacizumab | Avastin ™ |
| interferon beta-1a; recombinant | Avonex ® |
| coagulation factor IX | BeneFix ™ |
| Interferon beta-1b | Betaseron ® |
| Tositumomab | Bexxar ® |
| antihemophilic factor | Bioclate ™ |
| human growth hormone | BioTropin ™ |
| botulinum toxin type A | Botox ® |
| alemtuzumab | Campath ® |
| acritumomab; technetium-99 labeled | CEA-Scan ® |
| alglucerase; modified form of beta-glucocerebrosidase | Ceredase ® |
| imiglucerase | Cerezyme ® |
| crotalidae polyvalent immune Fab, ovine | CroFab ™ |
| digoxin immune Fab, ovine | DigiFab ™ |
| rasburicase | Elitek ® |
| etanercept | Enbrel ® |
| epoetin alfa | Epogen ® |
| cetuximab | Erbitux ™ |

TABLE 5-continued

| Protein Product | Reference Drug |
| --- | --- |
| algasidase beta | Fabrazyme ® |
| urofollitropin | Fertinex ™ |
| follitropin beta | Follistim ™ |
| teriparatide | Forteo ® |
| human somatropin | GenoTropin ® |
| glucagon | GlucaGen ® |
| follitropin alfa | Gonal-F ® |
| antihemophilic factor | Helixate ® |
| Antihemophilic Factor; Factor XIII | Hemofil ® |
| insulin | Humalog ® |
| antihemophilic factor/von Willebrand factor complex | Humate-P ® |
| somatotropin | Humatrope ® |
| adalimumab | HUMIRA ™ |
| human insulin | Humulin ® |
| recombinant human hyaluronidase | Hylenex ™ |
| interferon alfacon-1 | Infergen ® |
| Eptifibatide | Integrilin ™ |
| alpha-interferon | Intron A ® |
| palifermin | Kepivance |
| anakinra | Kineret ™ |
| antihemophilic factor | Kogenate ®FS |
| insulin glargine | Lantus ® |
| granulocyte macrophage colony-stimulating factor | Leukine ®/ Leukine ® Liquid |
| lutropin alfa, for injection | Luveris |
| OspA lipoprotein | LYMErix ™ |
| ranibizumab | Lucentis ® |
| gemtuzumab ozogamicin | Mylotarg ™ |
| galsulfase | Naglazyme ™ |
| nesiritide | Natrecor ® |
| pegfilgrastim | Neulasta ™ |
| oprelvekin | Neumega ® |
| filgrastim | Neupogen ® |
| fanolesomab | NeutroSpec ™ (formerly LeuTech ®) |
| somatropin [rDNA] | Norditropin ®/ Norditropin Nordiflex ® |
| insulin; zinc suspension; | Novolin L ® |
| insulin; isophane suspension | Novolin N ® |
| insulin, regular; | Novolin R ® |
| insulin | Novolin ® |
| coagulation factor VIIa | NovoSeven ® |
| somatropin | Nutropin ® |
| immunoglobulin intravenous | Octagam ® |
| PEG-L-asparaginase | Oncaspar ® |
| abatacept, fully human soluable fusion protein | Orencia ™ |
| muromomab-CD3 | Orthoclone OKT3 ® |
| human chorionic gonadotropin | Ovidrel ® |
| peginterferon alfa-2a | Pegasys ® |
| pegylated version of interferon alfa-2b | PEG-Intron ™ |
| Abarelix; gonadotropin-releasing hormone antagonist | Plenaxis ™ |
| epoietin alfa | Procrit ® |
| aldesleukin | Proleukin, IL-2 ® |
| somatrem | Protropin ® |
| dornase alfa | Pulmozyme ® |
| Efalizumab; selective, reversible T-cell blocker | Raptiva ™ |
| combination of ribavirin and alpha interferon | Rebetron ™ |
| Interferon beta 1a | Rebif ® |
| antihemophilic factor | Recombinate ® |
| rAHF/ntihemophilic factor | ReFacto ® |
| lepirudin | Refludan ® |
| infliximab | Remicade ® |
| abciximab | ReoPro ™ |
| reteplase | Retavase ™ |
| rituximab | Rituxan ™ |
| interferon alfa-2a | Roferon-A ® |
| somatropin | Saizen ® |
| synthetic porcine secretin | SecreFlo ™ |
| basiliximab | Simulect ® |
| eculizumab | Soliris ® |

TABLE 5-continued

| Protein Product | Reference Drug |
| --- | --- |
| pegvisomant | Somavert ® |
| Palivizumab; recombinantly produced, humanized mAb | Synagis ™ |
| thyrotropin alfa | Thyrogen ® |
| tenecteplase | TNKase ™ |
| natalizumab | Tysabri ® |
| human immune globulin intravenous | Venoglobulin-S ® |
| interferon alfa-n1, lymphoblastoid | Wellferon ® |
| drotrecogin alfa | Xigris ™ |
| Omalizumab | Xolair ® |
| daclizumab | Zenapax ® |
| ibritumomab tiuxetan | Zevalin ™ |
| Somatotropin | Zorbtive ™ (Serostim ®) |

Other features and advantages of the invention will be apparent from the following detailed description, and from the claims.

This invention is further illustrated by the following examples that should not be construed as limiting. The contents of all references, patents and published patent applications cited throughout this application are incorporated herein by reference.

EXAMPLES

Example 1 cDNA Cloning of Ggta1 from *Cricetulus griseus* Tissues and from CHO Cells

Original oligonucleotide primer sets were designed (see, e.g., Table 2) based on homology to either the rat or mouse Ggta1 coding sequence. Initial repeated attempts to use these primers to amplify by PCR at least a partial Ggta1 sequence from CHO cell-derived cDNA or genomic DNA (gDNA) were unsuccessful. The present invention therefore encompasses the recognition that standard hybridization approaches may be insufficient to permit cloning of CHO Ggta1.

Specifically, a subset of these same primer sets was used to screen four tissue-specific cDNA pools derived from Chinese Hamster (rather than from a CHO cell line): brain, spleen, kidney, and ovary. These cDNA pools were derived from two separate, gender-differentiated animals (cDNA brain and spleen pools from a male Chinese hamster and cDNA kidney and ovary pool from a female Chinese hamster). cDNA pools were validated by PCR as being specific to Chinese hamster using a set of oligonucleotide primers complementary to a known, control CHO-specific gene sequence. All four cDNA pools resulted in the amplification of a specific 1.1 kb product (see FIG. 1). The PCR products were confirmed by DNA sequencing to correspond to the putative Chinese hamster ortholog of Ggta1 based on sequence homology to the mouse and rat Ggta1 translated sequences (FIG. 2).

The coding sequence of the Chinese hamster Ggta1 from ovary (referred to herein as Ggta1-a) is shown as SEQ ID NO:1 and its amino acid sequence as SEQ ID NO:2 in FIG. 3. The coding sequence of the Chinese hamster Ggta1 from spleen (referred to herein as Ggta1-b) is shown as SEQ ID NO:3 and its amino acid sequence as SEQ ID NO:4 in FIG. 4. As described above, these two sequences were derived from separate Chinese hamster "donors" (namely female and male). The two clones appear to be full length and include all the predicted exons (4 through 9) based on a comparison to the exon structure of the mouse Ggta1 gene.

The Ggta1-a and Ggta1-b coding sequences are greater than 99% identical to each other, with only 6 nucleotides diverging out of the 1110 bp coding sequence. Five of these nucleotide differences are silent; only one results in a conservative amino acid change (Ile69Val). Accordingly, the Ggta1-a and Ggta1-b amino acid sequences are greater than 99.5% identical.

The Ggta1-a and Ggta1-b nucleotide sequences are 79.4 and 79.6% identical, respectively, to the rat sequence; 87.2% and 87.5% identical, respectively, to the mouse sequence; 77.5% and 77.7% identical, respectively, to the cow sequence, and 82.2% and 82.3% identical, respectively, to the dog sequence. At the amino acid level, the Ggta1-a and Ggta1-b sequences are 81% identical to the rat sequence; 86% identical to the mouse sequence, 73% identical to the cow sequence, and 77% identical to the dog sequence.

The most highly conserved regions are those putatively required for ligand binding and catalytic activity, corresponding to amino acid residues Iso-82 to Val-370 of SEQ ID NO:2 or 4. (See *Biochimica et Biophysica Acta* (2000) 1480:222-234). See FIG. 2. At the amino acid level, the Ggta1-a and Ggta1-b sequences are 91% identical to the rat sequence; 90.3% identical to the mouse sequence, 83% identical to the cow sequence, and 79% identical to the dog sequence over the catalytic region. The Ggta1-a and Ggta1-b catalytic regions are greater than 95% identical to the Ggta1-c catalytic region.

Similar to the mouse and the rat gene sequences, alternative splicing of the Chinese hamster Ggta1 gene was also noted (data not shown). In particular, it appears that in at least one clone, exon 6 was excised (corresponding to Iso-40 to Gly-60 of SEQ ID NO:2). This deletion was discernable by PCR which resulted in a smaller amplified DNA fragment when visualized by agarose gel electrophoresis (note the doublet in FIG. 1, lanes 3-6).

Based on the above-described Chinese hamster Ggta1 sequences derived from tissue-specific DNA pools, additional qPCR oligonucleotide primer sets were designed with the intent of using them to amplify by PCR a Ggta1 from cDNA generated from a CHO cell line. Efforts to do so, however, were not initially successful. More surprisingly, these primers also failed to amplify any genomic copies of the gene (when using genomic DNA isolated from the same CHO cell source that was used for the cDNA screening). Without wishing to be bound by any particular theory, the present inventors proposed that the problem might result from DNA sequence heterogeneity present in the genomic copy of the CHO cell line Ggta1 gene in comparison to the genome of the parental Chinese hamster from which the cDNA pools (used to clone Ggta1-a and Ggta1-b sequences) were independently derived. In addition, exon 9, which encodes the majority of the catalytic region, exhibited characteristics which initially led us to believe it was toxic to *E. coli* (the bacterial cells used for cloning), further challenging successful cloning efforts from CHO cells.

Successful amplification from the CHO cell genomic DNA (gDNA) of a partial gene sequence of 5,877 base pairs and comprised of exons 8, 9 (and intervening intron) was ultimately achieved using a rationally designed set of PCR primers (Table 2). This partial Ggta1 genomic sequence is shown in FIG. 5 (SEQ ID NO:5), and the corresponding amino acid sequence in FIG. 6 (SEQ ID NO:7). A sequence analysis of several clones confirmed the presence of DNA polymorphisms (relative to the original Ggta1-a and Ggta1-b sequences). In particular, 13 amino acid changes (out of 275 residues) were noted in the exon 8-9 region of the Ggta1 gene relative to the sequence originally cloned from the ovary-derived cDNA Chinese hamster cDNA pool. This polymorphism equates to approximately a 5% difference in protein sequence (6.5% difference at the nucleotide level) when comparing the two gene sequences. In contrast, an unrelated, control CHO sequence likewise amplified by PCR from the four tissue-specific Chinese hamster cDNA pools all exhibited 100% base pair identity when compared directly with the CHO cell-derived cDNA sequence. This observation suggests a gene-specific bias in genetic polymorphisms.

In summary, the cloning of Ggta1 from CHO cells was technically challenging. While Ggta1 gene sequences for several species, including mouse, rat, cow, pig, dog, cat, and several others, were publicly accessible, the use of these related sequences to obtain the Ggta1 gene from CHO cells by routine homology cloning was not successful. Coupled with the lack of support in the literature for the presence of a Ggta1 activity in CHO cells, others might have then concluded that a CHO Ggta1 did not exist. Instead, the inventors recognized the sources of problems that they encountered, and pursued cloning of Ggta1 genes from Chinese hamster tissues and genomic DNA in order to provide the tools to ultimately allow the cloning of Ggta1 cDNA from CHO cells. Among other things, the challenges presented to researchers investigating cloning Ggta1 cDNA from CHO cells included (1) general consensus in the literature that CHO cells did not include the Ggta1 activity; (2) unusual divergence of DNA sequence homology between rodent sequences (e.g., mouse vs. rat in which the two respective Ggta1 gene sequences diverge by approximately 9%); and (3) genetic polymorphisms of the CHO cell Ggta1 gene sequence. The present inventors identified these challenges, developed strategies to meet them, and successfully cloned CHO Ggta1 sequences.

Example 2

Use of Transcriptional Profiling by qPCR to Screen for Differential Expression of the Ggta1 Gene in CHO Cell Line Clones The successful use of PCR requires stringent considerations, namely the use of carefully designed oligonucleotide primers with complementary nucleotide sequences to the target gene sequence being detected. The design of these sequence-matching primers for specifically profiling Ggta1 gene expression in CHO cells initially was not possible without first determining the exact sequence of the CHO Ggta1 gene, as described above. Based on knowledge of the cloned CHO cell Ggta1 sequence as described above, additional primers were then carefully designed to quantify by qPCR the relative expression levels of Ggta1 genes in clonal population of CHO cells expressing CTLA4-Ig. These primers were designed to specifically hybridize in a region of the Ggta1 exon 9 sequence shown through a multiple sequence alignment to be absolutely conserved in their respective nucleotide sequences (Table 2). The primers were qualified based on efficiency, specificity and sensitivity using a control DNA template. The dynamic range of these primers exceeded 8 orders of magnitude, indicating their ability in principle to detect Ggta1 mRNA levels down to the single-digit copy per cell.

Figure 7A:
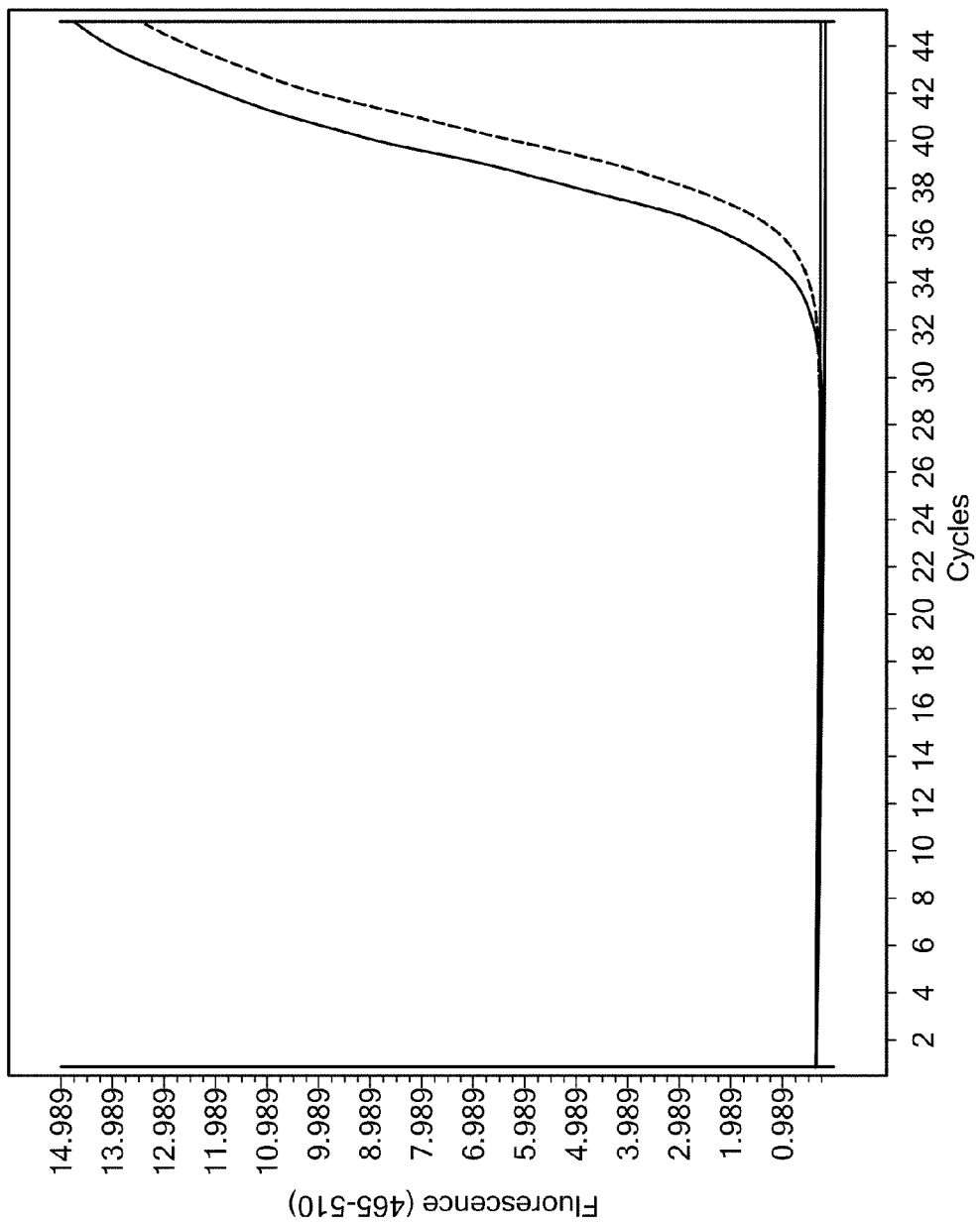
FIG. 7 shows PCR cycling profiles of select clones screened by qPCR to assess differential expression of the Ggta1 gene in CHO cell line clones (7A) and Tm analysis as assessment of primer specificity (7B).
Figure 7B:
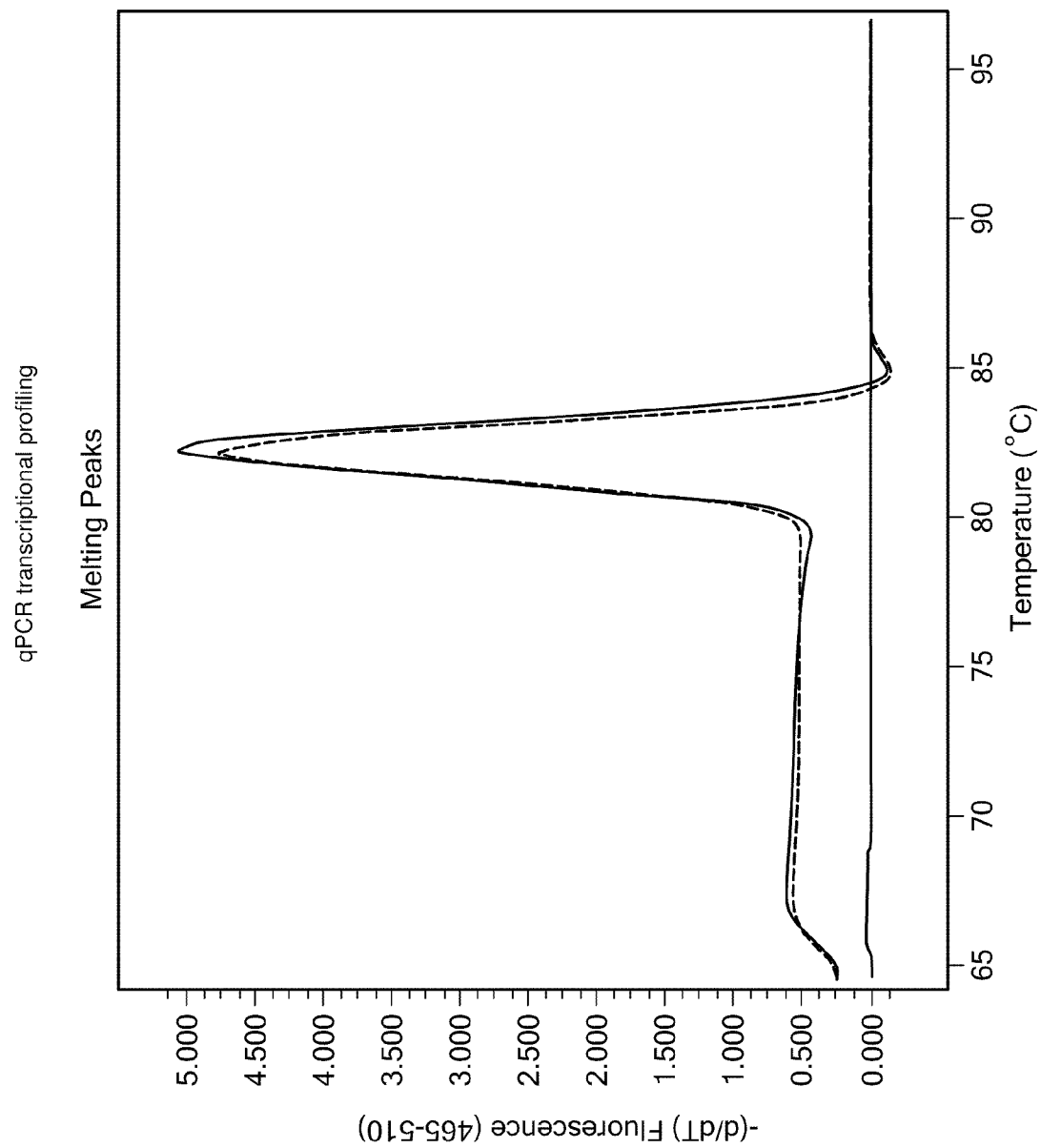

The qPCR results are summarized in FIG. 7. Clones were isolated by dilution following DHFR-based amplification of a CHO cell line expressing CTLA4-Ig. Ggta1 expression was quantified by qPCR using Exon 9 specific primers 845 (forward) and 846 (reverse) (sequences shown in Table 2). FIG. 7A shows the PCR cycling profiles of select clones. FIG. 7B shows an assessment of primer specificity by Tm analysis. Table 3 illustrates cycle threshold (Ct) values for three illustrative clones. These results indicate the amplification of a specific product (based on melting temperature analysis of the amplified product, FIG. 7B). Moreover, these results also demonstrate the use of these primers to differentiate unique clones derived from a single, parental CHO cell line based on relative expression levels of the Ggta1 gene (Table 3).

Figure 8:
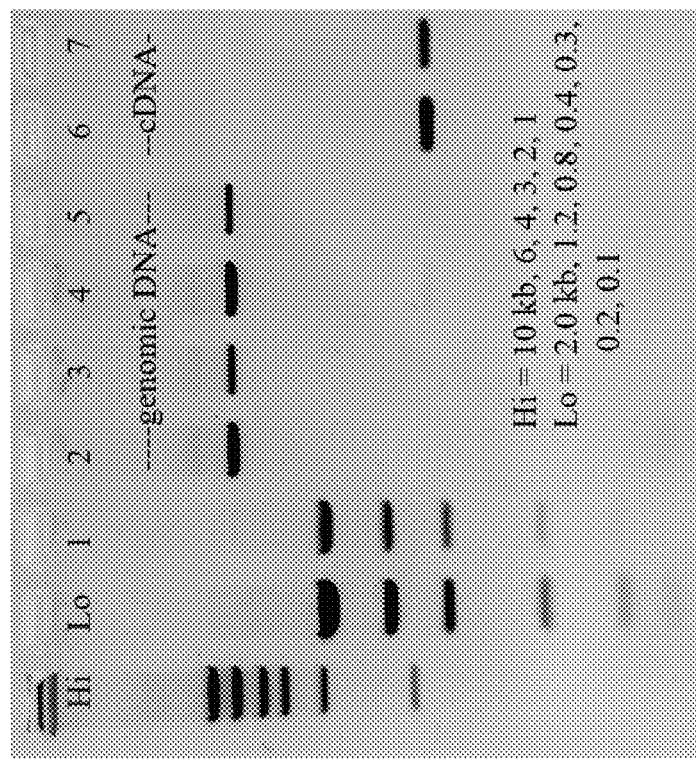
FIG. 8 is a photograph of an agarose gel electrophoretic separation of amplified Ggta1 PCR products. Primers 863 and 830 were used to amplify genomic DNA from CHO (DHFR-) cell line (lanes 2-5) or cDNA derived from same cell line (lanes 6 and 7).
Figure 9:
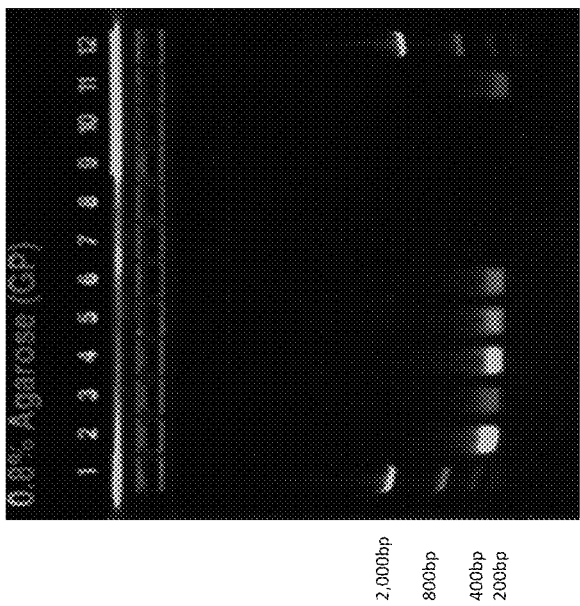
FIG. 9 is a photograph of an agarose gel electrophoretic separation of amplified Ggta1 PCR products. Ggta1-specific primers 875 (forward) and 855 (reverse) spanning two exons (exon 8 and 9) and designed to differentiate between expressed gene and genomic copies were used to profile three different amplified clones of DHFR-CHO cell line expressing CTLA4-Ig. Clones were isolated by dilution following amplification by methotrexate. Expected size of the Ggta1 PCR product (amplified specifically from cDNA) is 324 bp.

In addition, we designed primers that differentiate between genomic vs. transcriptional (cDNA) copies of the Ggta1 gene by mapping to adjoining exons (i.e., forward primer, exon 8; reverse primer, exon 9). The differential amplification of Ggta1 sequence corresponding to cDNA template vs. a genomic DNA (gDNA) template is illustrated in FIG. 8. These primers sets will not amplify genomic copies of Ggta1 under the qPCR conditions used due to the presence of a large (>5 kb), intervening intron sequence that physically separates the two exons in the genomic copy but is subsequently spliced out to form the mature Ggta1 mRNA transcript. Other primers disclosed herein were likewise used to screen CHO cell clones for differential expression of the Ggta1 gene. FIG. 9 shows the Ggta1 PCR product (amplified specifically from cDNA) is 324 bp. Such primers have particular value in certain applications such as the need to unequivocally detect and/or quantify low Ggta1 gene expression levels in a specific manner that excludes any potential for a false positive result due to genomic DNA carryover.

TABLE 2

Ggta1 oligonucleotide primers used for cloning and transcriptional profiling

| Purpose | Primer set | Sequence |
|---|---|---|
| cDNA cloning of full-length Ggta1 coding sequence from Chinese hamster tissues | 807 (forward) | TGGATCACAGGAGAAA ATAATGAA (SEQ ID NO: 8) |
| | 806 (reverse) | AAGTTTCCATCACAATT TGAAGTCAGA (SEQ ID NO: 9) |
| Cloning of Ggta1 gene sequence (exon 8, 9 and intron) from CHO cell genomic DNA | 863 (forward) | GAACCGCCCAGAAGTTT TGACAGTGACC (SEQ ID NO: 10) |
| | 830 (reverse) | GTCAGACATTACTCCTA ACCAAATTATAC (SEQ ID NO: 11) |
| Transcriptional profiling of Ggta1 expression in CHO cell line | 845 (forward) | ATGCCTCCAGAATGCCT TT (SEQ ID NO: 12) |
| | 846 (reverse) | ATCCACGTCCATACAGAA GA (SEQ ID NO: 13) |
| | 875 (forward) | GCCAGACAGAAAATCAC CG (SEQ ID NO: 14) |
| | 855 (reverse) | AAAGACCTGATCCACGTCC AT (SEQ ID NO: 15) |
| | 897 (forward) | TGGGAAGGCACTTATGAC AG (SEQ ID NO: 16) |
| | 892 (reverse) | TTGTAAGGAATGCAGAGG AC (SEQ ID NO: 17) |

TABLE 3

Ct values from illustrative clones screened by qPCR using primers 845 and 846

| Primer pairs | Clone 33 | Clone 33 (No RT) | Clone 34 | Clone 34 (No RT) | Clone 57 | Clone 57 (No RT) |
|---|---|---|---|---|---|---|
| pr845 + pr846 | 32.74 | ND | 34.26 | ND | ND | ND |

Clones were obtained by dilution from MTX amplified DHFR-CHO cell line expressing CTLA4-Ig;
No RT = minus reverse transcriptase control to rule out amplification from genomic copies of the Ggta1 gene;
ND = not detected

TABLE 4 exemplary oligonucleotides/primers/probes

| name | sequence | strand | nt | source |
|---|---|---|---|---|
| pr854 | GATGCCTCCAGAATGCCTT (SEQ ID NO: 18) | forward | 19 | CHO1 |
| pr874 | CTCATTCTTGAAGCTATGCC (SEQ ID NO: 19) | forward | 20 | CHO1 |
| pr875 | GCCAGACAGAAAATCACCG (SEQ ID NO: 20) | forward | 19 | CHO1 |
| pr876 | CTTACGGGACACATGCTA (SEQ ID NO: 21) | reverse | 19 | CHO1 |
| pr877 | GGCACAGAAGGGAAAGAC (SEQ ID NO: 22) | forward | 18 | CHO1 |
| pr878 | GTCAACCATCTAAGCTACAGT (SEQ ID NO: 23) | reverse | 21 | CHO1 |
| pr886 | AAATCTGACCCTAATCCTGTG (SEQ ID NO: 24) | forward | 21 | CHO1 |
| pr887 | CTCCTTGCTTTCTATGGCTT (SEQ ID NO: 25) | reverse | 20 | CHO1 |
| pr888 | GCCAGACAGAAAATCACC (SEQ ID NO: 26) | forward | 18 | CHO1 |
| pr895 | GTCTCCTTCCTAGTAACTCAAA (SEQ ID NO: 27) | reverse | 22 | CHO1 |
| pr896 | CTAGCATGTGTCCCCGTAA (SEQ ID NO: 28) | forward | 19 | CHO1 |
| pr898 | GCTGGTGGTTCCCGAG (SEQ ID NO: 29) | forward | 16 | CHO1 |
| pr855 | AAAGACCTGATCCACGTCCAT (SEQ ID NO: 30) | reverse | 21 | Exon8-9 |
| pr889 | GAAGTTTTGACAGTGACCCC (SEQ ID NO: 31) | forward | 20 | Exon8-9 |
| pr891 | GTTTTTGCTGTGGGAAAGTACAT (SEQ ID NO: 32) | forward | 23 | Exon8-9 |
| pr892 | TTGTAAGGAATGCAGAGGAC (SEQ ID NO: 33) | reverse | 20 | Exon8-9 |
| pr893 | AAAGACCTGATCCACGTCCA (SEQ ID NO: 34) | reverse | 20 | Exon8-9 |
| pr894 | GATCTCAAACACTTGTAAGGAATG (SEQ ID NO: 35) | reverse | 24 | Exon8-9 |
| pr897 | TGGGAAGGCACTTATGACAG (SEQ ID NO: 36) | forward | 20 | Exon8-9 |
| pr822 | AAATTCCAGAGATTGGTGACAGC (SEQ ID NO: 37) | forward | 23 | CH ovary |
| pr823 | GTCATAAGTGCCTTCCCACAC (SEQ ID NO: 38) | reverse | 21 | CH ovary |
| pr824 | TTATTACCACGCAGCCATTT (SEQ ID NO: 39) | forward | 20 | CH ovary |
| pr825 | TTCCATCACAATTTGAAGTCAGA (SEQ ID NO: 40) | reverse | 23 | CH ovary |
| pr830 | GTCAGACATTACTCCTAACCAAATTATAC (SEQ ID NO: 41) | reverse | 43 | CH ovary |
| pr831 | AATGAATGTCAAGGGAAAAGTGGTC (SEQ ID NO: 42) | forward | 36 | CH ovary |
| pr842 | TGATAGTCCCAACAGTACTCT (SEQ ID NO: 43) | reverse | 21 | CH ovary |
| pr843 | CACATCCTGACCCACATACA (SEQ ID NO: 44) | forward | 20 | CH ovary |
| pr844 | GACAGTTCCCGCCTCTCATA (SEQ ID NO: 45) | reverse | 20 | CH ovary |
| pr845 | ATGCCTCCAGAATGCCTTT (SEQ ID NO: 46) | forward | 19 | CH ovary |
| pr846 | ATCCACGTCCATACAGAAGA (SEQ ID NO: 47) | reverse | 20 | CH ovary |
| pr849 | GTACATTGAGCATTATTTGGAAG (SEQ ID NO: 48) | forward | 23 | CH ovary |
| pr850 | GTACATCGAGCATTATTTGGAAG (SEQ ID NO: 49) | forward | 23 | CH ovary |
| pr863 | GAACCGCCCAGAAGTTTTGACAGTGACC (SEQ ID NO: 50) | forward | 42 | CH ovary |
| pr899 | GCTGGTGGTTCCCGAG (SEQ ID NO:51) | forward | 30 | CH ovary |
| pr900 | GTCTCCTTCCTAGTAACTCAAA (SEQ ID NO: 52) | reverse | 36 | CH ovary |
| pr922 | ATGAAAATTCCAGAGATTGGTGA (SEQ ID NO: 53) | forward | 35 | CH ovary |
| pr923 | GGGcACCCACAGTTATCAAGAA (SEQ ID NO: 54) | forward | 36 | CH ovary |
| pr924 | GTCAGAATTGAgGAGCCTCACTT (SEQ ID NO: 55) | forward | 38 | CH ovary |

Extensions and Alternatives

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls. The section headings used herein are for organizational purposes only and are not to be construed as limiting the subject matter described in any way. While the methods have been described in conjunction with various embodiments and examples, it is not intended that the methods be limited to such embodiments or examples. On the contrary, the methods encompass various alternatives, modifications, and equivalents, as will be appreciated by those of skill in the art.

I claim:

1. A cDNA molecule comprising
   (i) a nucleic acid having at least 95% identity to a nucleotide sequence encoding the amino acid sequence of SEQ ID NO: 2, wherein the nucleic acid encodes a polypeptide that catalyzes synthesis of a Gal-α1,3-Gal glycan;
   (ii) a nucleic acid having at least 96% identity to a nucleotide sequence encoding the amino acid sequence of SEQ ID NO: 4, wherein the nucleic acid encodes a polypeptide that catalyzes synthesis of Gal-α1,3-Gal glycan;
   (iii) a nucleic acid having at least 99% identity to a nucleotide sequence encoding the amino acid sequence of SEQ ID NO: 7, wherein the nucleic acid encodes a polypeptide that catalyzes Gal-α1,3-Gal glycan; or
   (iv) the complement of the nucleic acid of (i), (ii), or (iii).

2. The cDNA molecule of claim 1, wherein the cDNA molecule comprises (v) a nucleic acid having at least 96% identity to a nucleotide sequence encoding the amino acid sequence of SEQ ID NO:2, or (vi) the complement of the nucleic acid of (v).

3. The cDNA molecule of claim 1, wherein the cDNA molecule comprises (v) a nucleic acid having at least 97% identity to a nucleotide sequence encoding the amino acid sequence of SEQ ID NO:2, or (vi) the complement of the nucleic acid of (v).

4. The cDNA molecule of claim 1, wherein the cDNA molecule comprises (v) a nucleic acid having at least 98% identity to a nucleotide sequence encoding the amino acid sequence of SEQ ID NO:2, or (vi) the complement of the nucleic acid of (v).

5. The cDNA molecule of claim 1, wherein the cDNA molecule comprises (v) a nucleic acid having at least 99% identity to a nucleotide sequence encoding the amino acid sequence of SEQ ID NO:2, or (vi) the complement of the nucleic acid of (v).

6. The cDNA molecule of claim 1, wherein the cDNA molecule comprises (v) a nucleic acid having at least 97% identity to a nucleotide sequence encoding the amino acid sequence of SEQ ID NO:4, or (vi) the complement of the nucleic acid of (v).

7. The cDNA molecule of claim 1, wherein the cDNA molecule comprises (v) a nucleic acid having at least 98% identity to a nucleotide sequence encoding the amino acid sequence of SEQ ID NO:4, or (vi) the complement of the nucleic acid of (v).

8. The cDNA molecule of claim 1, wherein the cDNA molecule comprises (v) a nucleic acid having at least 99% identity to a nucleotide sequence encoding the amino acid sequence of SEQ ID NO:4, or (vi) the complement of the nucleic acid of (v).

9. A cDNA molecule encoding the sequence of SEQ ID NO: 2, or SEQ ID NO:4 or SEQ ID NO:7.

10. A cDNA molecule having at least 90% sequence identity to the sequence of SEQ ID NO:1 or SEQ ID NO:3 or SEQ ID NO:6, wherein the cDNA encodes a polypeptide that catalyzes synthesis of a Gal-α1,3-Gal glycan.

11. A cDNA molecule comprising the nucleotide sequence of SEQ ID NO:1 or SEQ ID NO:3, SEQ ID NO:5 or SEQ ID NO:6, or a complement thereof.

12. A nucleic acid molecule comprising the cDNA molecule of any one of claims 10 and 11, linked in-frame to a nucleic acid encoding a heterologous amino acid sequence.

13. A nucleic acid construct comprising the sequence of the cDNA molecule of claim 1.

14. A vector comprising the cDNA molecule of claim 1.

15. A two dimensional array having a plurality of addresses, each address of the plurality being positionally distinguishable from each other address of the plurality, and each address of the plurality having a unique capture probe, wherein at least one address of the plurality has a capture probe comprising a cDNA molecule of claim 9, 10, or 11.

16. An isolated host cell transfected with an expression vector comprising the cDNA molecule of any one of claims 10 and 11.

17. The isolated host cell of claim 16, wherein the host cell produces a recombinant therapeutic glycoprotein having increased levels of terminal galactose-α1,3-galactose glycans compared to the recombinant therapeutic glycoprotein produced by parent cells of the host cell.

18. The isolated host cell of claim 17, wherein the cell is a Chinese hamster ovary (CHO) cell engineered to express a recombinant therapeutic glycoprotein.

19. The isolated host cell of claim 16, wherein the host cell produces a recombinant therapeutic glycoprotein having lower levels of terminal galactose-α1,3-galactose glycans compared to the recombinant therapeutic glycoprotein produced by parent cells of the host cell.

20. The isolated host cell of claim 19, wherein the cell is a CHO cell engineered to express a recombinant therapeutic glycoprotein.

21. A method of modulating the glycan structure of a recombinant therapeutic glycoprotein produced in a CHO cell, the method comprising culturing the isolated host cell of claim 18 under conditions sufficient to express the recombinant therapeutic glycoprotein.

22. A method of modulating the glycan structure of a recombinant therapeutic glycoprotein produced in a CHO cell, the method comprising culturing the isolated host cell of claim 20 under conditions sufficient to express the recombinant therapeutic glycoprotein.

23. A method of detecting Ggta1 expression in a CHO cell population, the method comprising: hybridizing a nucleic acid sample from the CHO cell population with the cDNA molecule of claim 9, 10, or 11, wherein the cDNA molecule further comprises a label, to thereby detect Ggta1 expression in the CHO cell population.

24. A method of detecting Ggta1 expression in a CHO cell population, the method comprising obtaining a nucleic acid sample from the CHO cell population, amplifying a Ggta1 nucleic acid sequence in the nucleic acid sample using PCR, and detecting the amplified Ggta1 molecules with the cDNA molecule of claim 9, 10, or 11, wherein the cDNA molecule further comprises a label.

25. The method of claim 23, further comprising quantifying the level of Ggta1 expression in the CHO cell population.

26. The method of claim 25, further comprising comparing the level of Ggta1 expression in the CHO cell population to a reference level, a control level, a pre-determined level or a level exhibited by a second CHO cell population.

27. A method of analyzing a nucleic acid sample from a CHO cell, the method comprising contacting the nucleic acid sample to the array of claim 15.

\* \* \* \* \*

UNITED STATES PATENT AND TRADEMARK OFFICE
CERTIFICATE OF CORRECTION

PATENT NO. : 8,609,372 B2
APPLICATION NO. : 12/943719
DATED : December 17, 2013
INVENTOR(S) : James W. Meador, III It is certified that error appears in the above-identified patent and that said Letters Patent is hereby corrected as shown below:

In the Claims:

Column 66, line 29 (claim 11, line 2) delete "SEQ ID NO:5".

Column 66, line 32 (claim 12, line 2) delete "claims 10 and 11" and insert --claims 1 and 9-11-- therefore.

Column 66, line 43 (claim 15, line 6) delete "claim 9, 10, or 11" and insert --claim 1, 9, 10, or 11-- therefore.

Column 66, lines 45-46 (claim 16, lines 2-3) delete "claims 10 and 11" and insert --claims 1 and 9-11-- therefore.

Column 67, line 9 (claim 23, line 4) delete "claim 9, 10, or 11" and insert --claim 1, 9, 10, or 11-- therefore.

Column 67, line 17 (claim 24, line 6) delete "claim 9, 10, or 11" and insert --claim 1, 9, 10, or 11-- therefore.

Signed and Sealed this
Twenty-fifth Day of March, 2014

Michelle K. Lee
*Deputy Director of the United States Patent and Trademark Office*